US012746394B2

(12) United States Patent
Sheldon et al.

(10) Patent No.: US 12,746,394 B2
(45) Date of Patent: Sep. 29, 2026

(54) ATRIAL TRACKING CONFIRMATION IN AN INTRACARDIAC VENTRICULAR PACEMAKER

(71) Applicant: Medtronic, Inc., Minneapolis, MN (US)

(72) Inventors: Todd J. Sheldon, North Oaks, MN (US); Wade M. Demmer, Coon Rapids, MN (US); Gregory R. Herr, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 419 days.

(21) Appl. No.: 18/365,908

(22) Filed: Aug. 4, 2023

(65) Prior Publication Data

US 2023/0372716 A1 Nov. 23, 2023

Related U.S. Application Data

(63) Continuation of application No. 16/993,684, filed on Aug. 14, 2020, now Pat. No. 11,752,346, which is a (Continued)

(51) Int. Cl.
*A61N 1/365* (2006.01)
*A61B 5/00* (2006.01)

(Continued)

(52) U.S. Cl.
CPC ........ *A61N 1/36578* (2013.01); *A61B 5/1102* (2013.01); *A61B 5/352* (2021.01); *A61B 5/4836* (2013.01); *A61B 5/686* (2013.01); *A61B 5/7282* (2013.01); *A61N 1/3682* (2013.01); *A61N 1/37205* (2013.01); *A61N 1/3756* (2013.01);

(Continued)

(58) Field of Classification Search
CPC .............. A61N 1/36578; A61N 1/3682; A61B 5/1102; A61B 5/352
See application file for complete search history.

(56) References Cited

U.S. PATENT DOCUMENTS

| | | |
|---|---|---|
| 4,485,813 A | 12/1984 | Anderson et al. |
| 5,052,388 A | 10/1991 | Sivula et al. |

(Continued)

OTHER PUBLICATIONS (PCT/US2018/040989) PCT Notification of Transmittal of the International Search Report and the Written Opinion of the International Searching Authority, Mailed Sep. 24, 2018, 9 pages.

(Continued)

*Primary Examiner* — Amanda L Steinberg
*Assistant Examiner* — Philip C Edwards

(57) ABSTRACT

A pacemaker having a motion sensor delivers atrial-synchronized ventricular pacing by detecting events from a signal produced by the motion sensor and delivering ventricular pacing pulses at a rate that tracks the rate of the detected events. The pacemaker is configured to confirm atrial tracking of the ventricular pacing pulses by determining if detected events from the motion sensor signal are atrial events. The pacemaker is configured to adjust a control parameter used for detecting events from the motion sensor signal if atrial tracking is not confirmed.

20 Claims, 14 Drawing Sheets

Related U.S. Application Data continuation of application No. 16/027,717, filed on Jul. 5, 2018, now Pat. No. 10,744,329.

(60) Provisional application No. 62/529,609, filed on Jul. 7, 2017.

(51) Int. Cl.

| | |
|---|---|
| ***A61B 5/11*** | (2006.01) |
| ***A61B 5/352*** | (2021.01) |
| ***A61N 1/05*** | (2006.01) |
| ***A61N 1/368*** | (2006.01) |
| ***A61N 1/372*** | (2006.01) |
| ***A61N 1/375*** | (2006.01) |

(52) U.S. Cl.

CPC ........ *A61N 1/0573* (2013.01); *A61N 1/37217* (2013.01)

(56) References Cited

U.S. PATENT DOCUMENTS

| | | | | |
|---|---|---|---|---|
| 5,507,782 | A | 4/1996 | Kieval et al. | |
| 5,593,431 | A | 1/1997 | Sheldon | |
| 5,885,471 | A | 3/1999 | Ruben et al. | |
| 6,044,297 | A | 3/2000 | Sheldon et al. | |
| 8,433,409 | B2 | 4/2013 | Johnson et al. | |
| 8,532,785 | B1 | 9/2013 | Crutchfield et al. | |
| 8,541,131 | B2 | 9/2013 | Lund et al. | |
| 9,399,140 | B2 | 7/2016 | Cho et al. | |
| 10,286,214 | B2 | 5/2019 | Demmer et al. | |
| 10,449,366 | B2 | 10/2019 | Splett et al. | |
| 10,532,212 | B2 | 1/2020 | Splett et al. | |
| 10,864,377 | B2 | 12/2020 | Sheldon et al. | |
| 2012/0172892 | A1 | 7/2012 | Grubac et al. | |
| 2012/0172944 | A1 | 7/2012 | Dori et al. | |
| 2016/0023000 | A1* | 1/2016 | Cho | A61N 1/3621 607/18 |
| 2016/0067487 | A1 | 3/2016 | Demmer et al. | |
| 2016/0129263 | A1 | 5/2016 | Demmer et al. | |
| 2017/0056665 | A1 | 3/2017 | Kane et al. | |
| 2018/0085588 | A1* | 3/2018 | Splett | A61N 1/3682 |
| 2018/0085589 | A1* | 3/2018 | Splett | A61N 1/36542 |
| 2018/0117337 | A1* | 5/2018 | Demmer | A61N 1/36578 |
| 2018/0154154 | A1* | 6/2018 | Sheldon | A61N 1/3756 |

OTHER PUBLICATIONS

Chinese Communication dated Feb. 10, 2023, Chinese Patent Application No. 201880045303.1, 5 pages.

* cited by examiner

ATRIAL TRACKING CONFIRMATION IN AN INTRACARDIAC VENTRICULAR PACEMAKER

CROSS-REFERENCE TO RELATED APPLICATIONS

This application is a Continuation of U.S. patent application Ser. No. 16/993,684, filed Aug. 14, 2020, which is a Continuation of U.S. patent application Ser. No. 16/027,717, filed Jul. 5, 2018 and granted as U.S. Pat. No. 10,744,329, which claims the benefit of U.S. Provisional Application No. 62/529,609, filed Jul. 7, 2017, all of which are incorporated herein by reference in their entirety.

TECHNICAL FIELD

The disclosure relates to an intracardiac ventricular pacemaker and associated method for detecting atrial events from a motion sensor signal of the pacemaker and controlling ventricular pacing delivered by the pacemaker based on the detected atrial events.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, other conditions may require atrial and ventricular (dual chamber) sensing for providing atrial-synchronized ventricular pacing in order to maintain a regular heart rhythm.

SUMMARY

In general, the disclosure is directed to a ventricular pacemaker and techniques for confirming atrial-synchronized ventricular pacing by the ventricular pacemaker. An intracardiac ventricular pacemaker operating according to the techniques disclosed herein detects atrial events from a motion sensor signal and delivers ventricular pacing pulses synchronized to the detected atrial events. The pacemaker confirms that events being detected from the motion sensor signal and tracked by the ventricular pacing pulses are atrial events, attendant to atrial contractions, as opposed to being oversensed ventricular events in the motion sensor signal or other oversensed non-cardiac, motion sensor signal noise.

In one example, the disclosure provides an intracardiac ventricular pacemaker, including a pulse generator, a motion sensor and a control circuit. The motion sensor is configured to produce a motion signal including an atrial event attendant to atrial motion and at least one ventricular event attendant to ventricular motion during each cardiac cycle. The control circuit is configured to confirm atrial tracking of ventricular pacing pulses delivered by the pulse generator via electrodes coupled to the pacemaker. Atrial tracking is confirmed by detecting a first event from the motion sensor signal; setting an atrioventricular (AV) interval in response to detecting the first event; controlling the pulse generator to deliver a first ventricular pacing pulse in response to the AV interval expiring; withholding delivering a second ventricular pacing pulse following the first event; detecting a second event from the motion sensor signal following the first event; confirming that the first event is the atrial event in response to the second event occurring at least a threshold time interval since the first ventricular pacing pulse; and confirming atrial tracking of the ventricular pacing pulses in response to confirming that the first event is the atrial event.

In another example, the disclosure provides a method performed by an intracardiac ventricular pacemaker for confirming atrial tracking of pacing pulses delivered by the pacemaker, the pacemaker including a motion sensor configured to produce a signal including an atrial event attendant to atrial motion and at least one ventricular event attendant to ventricular motion during each cardiac cycle. The method includes detecting by a control circuit of the pacemaker a first event from the motion sensor signal; setting an AV interval in response to detecting the first event; controlling a pulse generator to deliver a first ventricular pacing pulse in response to the AV interval expiring; withholding delivering a second ventricular pacing pulse following the first event; detecting a second event from the motion sensor signal following the first event; confirming that the first event is the atrial event in response to the second event occurring at least a threshold time interval since the first ventricular pacing pulse; and confirming atrial tracking of the pacing pulses in response to confirming that the first event is the atrial event.

In yet another example, the disclosure provides a non-transitory computer-readable medium storing a set of instructions which when executed by a control circuit of an intracardiac ventricular pacemaker having a motion sensor, cause the pacemaker to confirm atrial tracking of pacing pulses delivered by the pacemaker by detecting a first event from the motion sensor signal; setting an AV interval in response to detecting the first event; delivering a first ventricular pacing pulse in response to the AV interval expiring; withholding delivering a second ventricular pacing pulse following the first event; detecting a second event from the motion sensor signal following the first event; confirming that the first event is the atrial event in response to the second event occurring at least a threshold time interval since the first ventricular pacing pulse; and confirming atrial tracking of pacing pulses delivered by the pacemaker in response to confirming that the first event is the atrial event.

In another example, the disclosure provides a pacemaker including a pulse generator configured to deliver pacing pulses to a ventricle of a patient's heart via electrodes coupled to the pacemaker, a motion sensor configured to produce a signal including an atrial event attendant to atrial motion and at least one ventricular event attendant to ventricular motion during each cardiac cycle; and a control circuit coupled to the motion sensor and the pulse generator and configured to detect events from the motion sensor signal. The control circuit is configured to control the pulse generator to deliver the pacing pulses at a rate that is tracked to the detected events. During an atrial-tracing confirmation process, the control circuit is configured to confirm whether the detected events from the motion sensor signal are atrial events. The control circuit is configured to return to the atrial-synchronized ventricular pacing mode in response to confirming that the detected events are the atrial events and adjusts a control parameter used in detecting events from the motion sensor signal in response to not confirming that the detected events are the atrial events.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
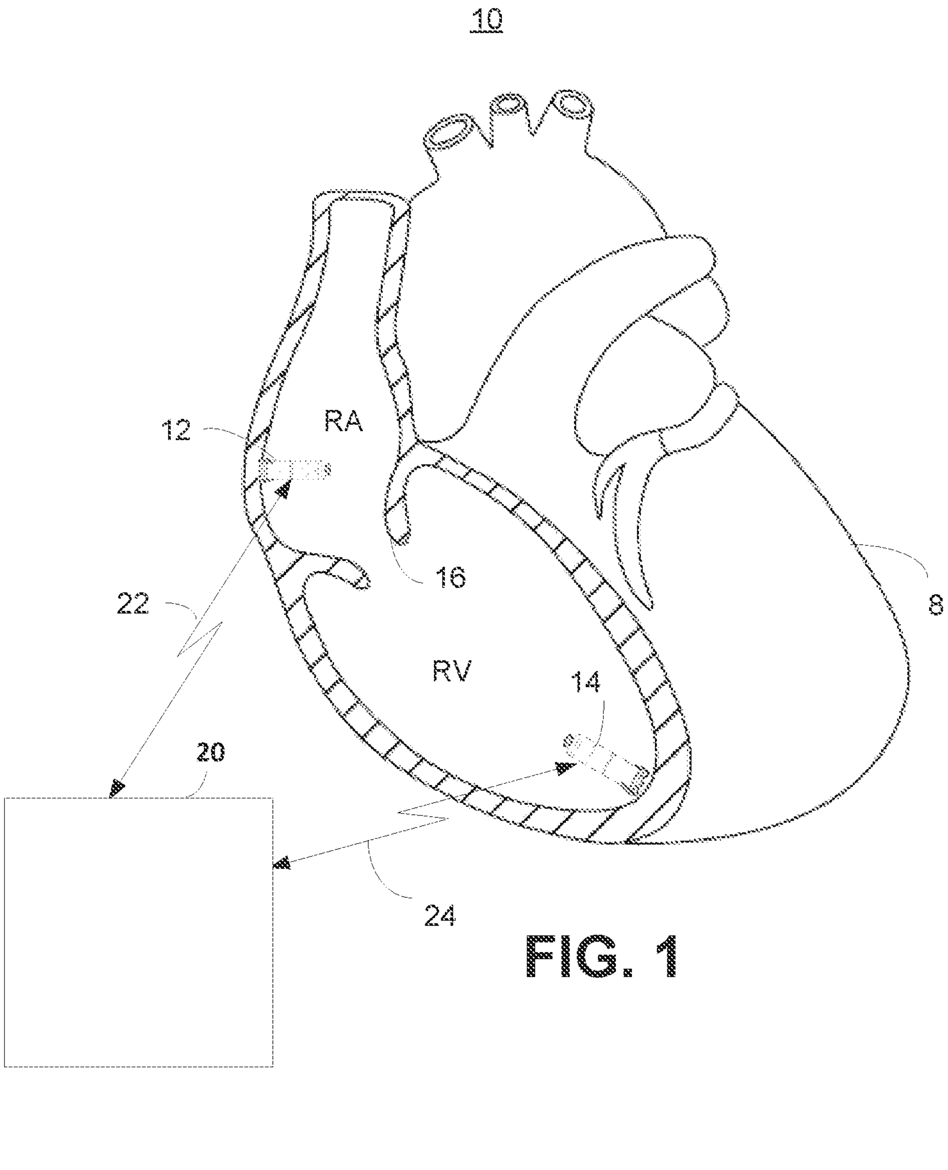
FIG. 1 is a conceptual diagram illustrating an intracardiac pacing system that may be used to sense cardiac electrical signals and motion signals induced by cardiac motion and flowing blood and provide pacing therapy to a patient's heart.

FIG. 1 is a conceptual diagram illustrating an intracardiac pacing system 10 that may be used to sense cardiac electrical signals and motion signals induced by cardiac motion and flowing blood and provide pacing therapy to a patient's heart 8. IMD system 10 includes a right ventricular (RV) intracardiac pacemaker 14 and may optionally include a right atrial (RA) intracardiac pacemaker 12 in some examples. Pacemakers 12 and 14 are transcatheter intracardiac pacemakers which may be adapted for implantation wholly within a heart chamber, e.g., wholly within the RV, wholly within the left ventricle (LV), wholly within the RA or wholly within the left atrium (LA) of heart 8.

In the example of FIG. 1, RA pacemaker 12 is positioned along an endocardial wall of the RA, e.g., along the RA lateral wall or RA septum. RV pacemaker 14 is positioned along an endocardial wall of the RV, e.g., near the RV apex though other locations are possible. The techniques disclosed herein are not limited to the pacemaker locations shown in the example of FIG. 1 and other positions and relative locations in the heart 8 and from each other are possible. For example, a intracardiac ventricular pacemaker 14 may be positioned in the LV for and configured to detect cardiac motion signals and deliver atrial-synchronized ventricular pacing to the LV using the techniques disclosed herein.

Pacemakers 12 and 14 are reduced in size compared to subcutaneously implanted pacemakers and may be generally cylindrical in shape to enable transvenous implantation via a delivery catheter. In other examples, pacemakers 12 and 14 may be positioned at any other location inside heart 8. For example, pacemaker 12 may be positioned outside or within the right atrium or left atrium to provide respective right atrial or left atrial pacing. Pacemaker 14 may be positioned within the right ventricle or left ventricle to provide respective right ventricular or left ventricular pacing and for sensing motion signals by a motion sensor within the ventricular chamber.

Pacemakers 12 and 14 are each capable of producing electrical stimulation pulses, e.g., pacing pulses, delivered to heart 8 via one or more electrodes on the outer housing of the pacemaker. RA pacemaker 12 is configured to sense a cardiac electrical signal from within the RA that may be used to produce an RA intracardiac electrogram (EGM) signal. RV pacemaker 14 is configured to deliver RV pacing pulses and sense an RV cardiac electrical signal using housing-based electrodes for producing an RV EGM signal. The cardiac electrical signals may be sensed by the respective pacemaker 12 or 14 using the housing-based electrodes that are also used to deliver pacing pulses to the respective RA or RV.

In some examples, a patient may only require RV pacemaker 14 for delivering ventricular pacing. In other examples, depending on individual patient need, RA pacemaker 12 may be required for delivering atrial pacing. The RV pacemaker 14 is configured to control the delivery of ventricular pacing pulses to the RV in a manner that promotes synchrony between the RA activation and the RV activation, e.g., by maintaining a target atrioventricular (AV) interval between atrial events and ventricular pacing pulses. That is, the RV pacemaker 14 controls RV pacing pulse delivery to maintain a desired AV interval between atrial activations (intrinsic or pacing-evoked) corresponding to atrial systole and ventricular pacing pulses delivered to cause ventricular depolarization.

According to the techniques described herein, atrial activations are detected by RV pacemaker 14 from a motion sensor signal that includes motion signals caused by ventricular and atrial events. For example, acceleration of blood flowing into the RV through the tricuspid valve 16 between the RA and RV caused by atrial activation, sometimes referred to as the "atrial kick," is detected by RV pacemaker 14 from the signal produced by a motion sensor, for example an accelerometer, included in RV pacemaker 14. Other motion signals detected by RV pacemaker 14, such as motion caused by ventricular contraction, motion caused by ventricular relaxation, and motion caused by passive filling of the ventricle are described below in conjunction with FIG. 4.

Atrial P-waves that are attendant to atrial depolarization are relatively low amplitude signals in the near-field RV cardiac electrical signal received by RV pacemaker 14 (e.g., compared to the near-field R-wave) and therefore can be difficult to reliably detect from the cardiac electrical signal acquired by RV pacemaker 14. As such, atrial-synchronized ventricular pacing by RV pacemaker 14 may not be reliable when based solely on a cardiac electrical signal received by RV pacemaker 14.

According to the techniques disclosed herein, the RV pacemaker 14 includes a motion sensor, such as an accelerometer, and is configured to detect an atrial event corresponding to atrial mechanical activation or atrial systole using a signal from the motion sensor. Ventricular pacing pulses are synchronized to the atrial event that is detected from the accelerometer signal by setting a programmable AV pacing interval that controls the timing of the ventricular pacing pulse relative to the detected atrial systolic event. As described below, detection of the atrial systolic event used to synchronize ventricular pacing pulses to atrial systole may include detection of other cardiac event motion signals in order to positively identify the atrial systolic event.

The techniques of this disclosure may be used to confirm that RV pacemaker 14 is properly tracking an atrial event, e.g., the atrial kick. For example, in some instances, RV pacemaker 14 may oversense the atrial event. That is, RV pacemaker may identify an atrial signal that does not correspond to the atrial kick as corresponding to the atrial kick. In such instances, RV pacemaker 14 may apply improper pacing pulses in an effort to achieve AV synchrony. According to aspects of this disclosure, RV pacemaker 14 may confirm that the motion signal identified as corresponding to an atrial event actually corresponds to the atrial event. RV pacemaker 14 may apply a therapy based on the confirmation. For example, RV pacemaker 14 may apply a ventricular pacing pulse that is synchronized with the atrial event in instances in which the atrial event is confirmed, or withhold a ventricular pacing pulse in instances in which the atrial event is not confirmed. In this way, the techniques may be used to interrupt tracking of oversensed, non-atrial activation events that may lead to an accelerated ventricular pacing rate and restore proper atrial event tracking of ventricular pacing pulses.

In general, a target AV interval may be a programmed value selected by a clinician and is the time interval from the detection of the atrial event until delivery of the ventricular pacing pulse. In some instances, the target AV interval may be started from the time the atrial systolic event is detected based on a motion sensor signal or starting from an identified fiducial point of the atrial event signal. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by RV pacemaker 14 and the motion sensor signal received by RV pacemaker 14.

Pacemakers 12 and 14 may each be capable of bidirectional wireless communication with an external device 20 for programming the AV pacing interval and other pacing control parameters as well as mechanical event sensing parameters utilized for detecting ventricular mechanical events and the atrial systolic event from the motion sensor signal. Aspects of external device 20 may generally correspond to the external programming/monitoring unit disclosed in U.S. Pat. No. 5,507,782 (Kieval, et al.). External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemakers 12 and 14 using external device 20.

External device 20 is configured for bidirectional communication with implantable telemetry circuitry included in RV pacemaker 14 and RA pacemaker 12 (when present). External device 20 establishes a wireless radio frequency (RF) communication link 22 with RA pacemaker 12 and wireless RF communication link 24 with RV pacemaker 14 using a communication protocol that appropriately addresses the targeted pacemaker 12 or 14. Communication links 22 and 24 may be established using an RF link such as BLUETOOTH®, Wi-Fi, Medical Implant Communication Service (MICS) or other communication bandwidth. In some examples, external device 20 may include a programming head that is placed proximate pacemaker 12 or 14 to establish and maintain a communication link, and in other examples external device 20 and pacemakers 12 and 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety.

External device 20 may display data and information relating to pacemaker functions to a user for reviewing pacemaker operation and programmed parameters as well as EGM signals transmitted from pacemaker 14 or pacemaker 12, motion sensor signals acquired by RV pacemaker 14, or other physiological data that is acquired by and retrieved from pacemakers 12 and/or 14 during an interrogation session.

It is contemplated that external device 20 may be in wired or wireless connection to a communications network via a telemetry circuit that includes a transceiver and antenna or via a hardwired communication line for transferring data to a remote database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in RV pacemaker 14, e.g., after viewing a visual representation of EGM, motion sensor signal and marker channel data.

RA pacemaker 12 and RV pacemaker 14 may or may not be configured to communicate directly with each other. When pacemakers 12 and 14 are configured to communicate with each other, communication may be minimized in order to conserve battery life of the intracardiac pacemakers 12 and 14. As such, communication may not occur on a beat-by-beat basis between the RA pacemaker 12 and RV pacemaker 14 for communicating when the other pacemaker is sensing cardiac events or when it is delivering pacing pulses. As disclosed herein, RV pacemaker 14, however, is configured to detect atrial events as often as beat-by-beat from a motion sensor signal, without requiring communication signals from RA pacemaker 12 to provide atrial event detection for controlling atrial-synchronized ventricular pacing.

Figure 2A:
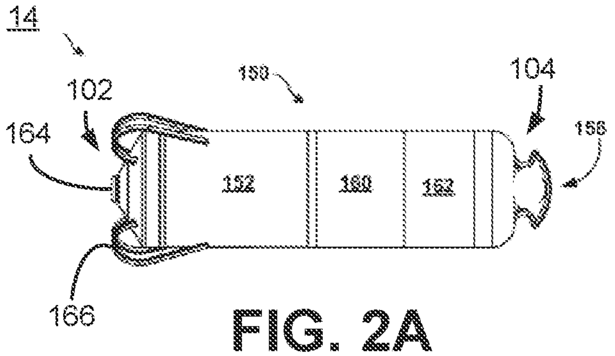
FIG. 2A is a conceptual diagram of the intracardiac ventricular pacemaker shown in FIG. 1.

FIG. 2A is a conceptual diagram of the intracardiac RV pacemaker 14 shown in FIG. 1. RV pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 as a ring electrode that is electrically isolated from the other portions of the housing 150 as generally shown in FIG. 2A. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting ventricular mechanical events and atrial systolic events for timing ventricular pacing pulses as described below.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Publication No. 2012/0172892, granted as U.S. Pat. No. 9,775,982 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 2B:
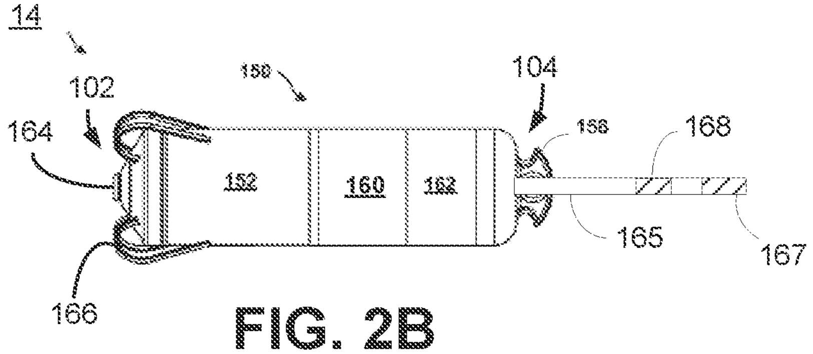
FIG. 2B is a conceptual diagram of another example of the intracardiac ventricular pacemaker shown in FIG. 1.

FIG. 2B is a conceptual diagram of another example of RV pacemaker 14. In FIG. 2B, RV pacemaker 14 includes a proximal sensing extension 165 extending away from housing 150 and carrying a pair of sensing electrodes 167 and 168. The proximal sensing extension 165 may be coupled to the housing 150 for positioning a return sensing electrode 168 or 167 which may be paired with distal electrode 164 at an increased inter-electrode distance compared to the inter-electrode spacing of housing-based electrodes 162 and 164. The increased inter-electrode distance may facilitate sensing of far-field atrial signals such as P-waves attendant to atrial depolarization.

Alternatively, electrodes 167 and 168 may form a sensing electrode pair for sensing atrial P-waves. When distal end 102 is fixed along the RV apex, sensing extension 165 may extend toward the RA thereby positioning electrodes 167 and 168 nearer the atrial tissue for sensing far-field atrial P-waves. One electrode 167 may be coupled to sensing circuitry enclosed in housing 150 via an electrical feedthrough crossing housing 150, and one electrode 168 may be coupled to housing 150 to serve as a ground electrode.

Figure 3:
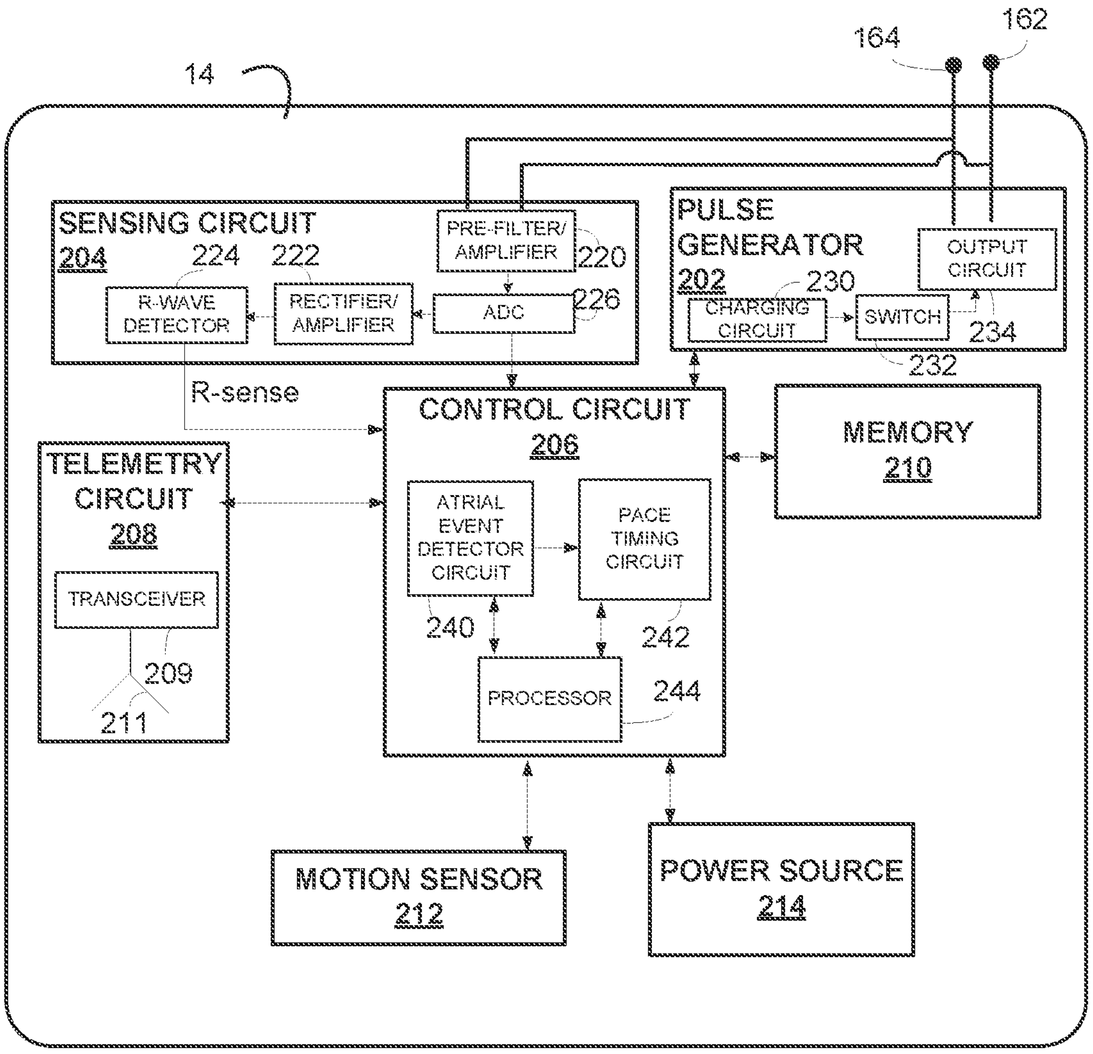
FIG. 3 is a schematic diagram of an example configuration of the pacemaker of FIG. 2A.

FIG. 3 is a schematic diagram of an example configuration of RV pacemaker 14 shown in FIG. 1. Pacemaker 14 includes a pulse generator 202, a sensing circuit 204, a control circuit 206, memory 210, telemetry circuit 208, motion sensor 212 and a power source 214. Motion sensor 212 is implemented as an accelerometer in the examples described herein and may also be referred to herein as "accelerometer 212." Motion sensor 212 is not limited to being an accelerometer, however, and other motion sensors may be utilized successfully in pacemaker 14 for detecting cardiac motion signals according to the techniques described herein. Examples of motion sensors that may be implemented in pacemaker 14 include piezoelectric sensors, micro electro-mechanical systems (MEMS) devices or other sensor elements capable of producing an electrical signal in response to changes in acceleration imparted on the sensor element, e.g., by converting the acceleration to a force or displacement that is converted to the electrical signal.

Motion sensor 212 may be a multi-axis sensor, e.g., a two-dimensional or three-dimensional sensor, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on RV pacemaker 14 due to ventricular and atrial events.

The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 includes an atrial event detector circuit 240, pace timing circuit 242, and processor 244. Atrial event detector circuit 240 is configured to detect atrial mechanical events from a signal received from motion sensor 212. As described below, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14 is operating in a non-atrial tracking ventricular pacing mode and for preventing ventricular asystole in the absence of a detected atrial event. R-wave sensed event signals may also be passed to atrial event detector circuit 240 for use in setting ventricular event detection windows and/or atrial event refractory periods, for example as shown and described in conjunction with FIG. 6.

Atrial event detector circuit 240 receives a motion signal from motion sensor 212 and starts an atrial refractory period in response to a ventricular electrical event, e.g., an R-wave sensed event signal from sensing circuit 204 or delivery of a pacing pulse by pulse generator 202. Atrial event detector circuit 240 determines if the motion sensor signal satisfies atrial mechanical event detection criteria outside of the atrial refractory period. The motion sensor signal during the atrial refractory period may be monitored by atrial event detector circuit 240 for the purposes of detecting ventricular mechanical events, which may be used for confirming or validating atrial systolic event detection and/or setting atrial systolic event detection control parameters as further described below, e.g., in conjunction with FIG. 10.

As such, ventricular mechanical event detection windows may be set during the atrial refractory period and may be set according to predetermined time intervals following identification of a ventricular electrical event. Atrial event detector circuit 240 may be configured to detect one or more ventricular mechanical events during respective ventricular event detection windows during the atrial refractory period. The timing and detection of the ventricular mechanical events may be used to update the atrial refractory period and/or an atrial systolic detection threshold amplitude and may be used to confirm detection of the atrial systolic event occurring subsequent to expected ventricular mechanical events.

Atrial event detector circuit 240 passes an atrial event detection signal to processor 244 and/or pace timing circuit 242. Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242. Techniques for controlling atrial-synchronized ventricular pacing using a motion sensor signal are generally disclosed in U.S. Pat. No. 9,399,140, (Yong, et al.), incorporated herein by reference in its entirety.

Pace timing circuit 242 may additionally include a lower rate (LR) pacing interval timer for controlling a minimum ventricular pacing rate in the absence of detected atrial events. For example, if an atrial systolic event is not detected from the motion sensor signal triggering a ventricular pacing pulse at the programmed AV pacing interval, a ventricular pacing pulse may be delivered by pulse generator 202 upon expiration of the LR pacing interval to prevent ventricular asystole and maintain a minimum ventricular rate.

Processor 244 may retrieve other programmable pacing control parameters, such as pacing pulse amplitude and pacing pulse width that are passed to pulse generator 202 for controlling pacing pulse delivery. In addition to providing control signals to pace timing circuit 242 and pulse generator 202 for controlling pacing pulse delivery, processor 244 may provide sensing control signals to sensing circuit 204, e.g., R-wave sensing threshold, sensitivity, various blanking and refractory intervals applied to the cardiac electrical signal, and atrial event detection control signals to atrial event detector circuit 240 for use in detecting and confirming atrial systolic events, e.g., ventricular event detection windows, atrial refractory period, detection threshold amplitudes applied to the motion sensor signal, and any other atrial event detection criteria applied by circuitry included in atrial event detector circuit 240.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modem pacemaker, given the disclosure herein, is within the abilities of one of skill in the art.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or LR pacing interval) and kept closed for a programmed pacing pulse duration to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the delivery of pacing pulses by pulse generator 202, e.g., by detecting an atrial systolic event by atrial event detector circuit 240 from the motion sensor signal and setting a pacing escape interval timer included in pace timing circuit 242, according to the techniques disclosed herein.

Power source 214 provides power to each of the other circuits and components of pacemaker 14 as required. Control circuit 206 may execute power control operations to control when various circuits or components are powered to perform various pacemaker functions. Power source 214 may include one or more energy storage devices, such as one or more rechargeable or non-rechargeable batteries. The connections between power source 214 and other pacemaker circuits and components are not shown in FIG. 3 for the sake of clarity.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

Figure 4:
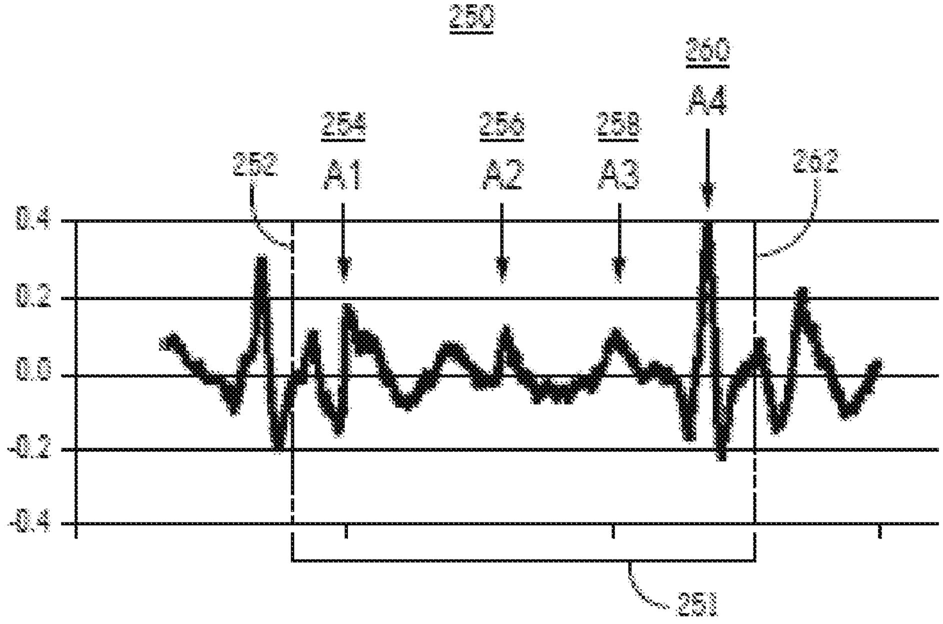
FIG. 4 is an example of a motion sensor signal that may be acquired over a cardiac cycle by a motion sensor included in the intracardiac ventricular pacemaker of FIG. 1.

FIG. 4 is an example of a motion sensor signal 250 that may be acquired by motion sensor 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 250 is implemented as an accelerometer) that occurs during ventricular contraction and marks the approximate onset of ventricular mechanical systole. The A1 event is also referred to herein as a "ventricular contraction event." The A2 event 265 is an acceleration signal that occurs during ventricular relaxation and marks the approximate offset or end of ventricular mechanical systole. The A2 event is also referred to herein as the "ventricular relaxation event." The A3 event 258 is an acceleration signal that occurs during passive ventricular filling and marks ventricular mechanical diastole. The A3 event is also referred to herein as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is also referred to herein as the "atrial systolic event" or merely the "atrial event," and is the atrial systolic event that is detected from motion sensor signal 250 by atrial event detector circuit 240 for controlling pace timing circuit 242 to trigger ventricular pacing pulse delivery by starting an AV pacing interval in response to detecting the A4 event 260. As described below, control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

Figure 5:
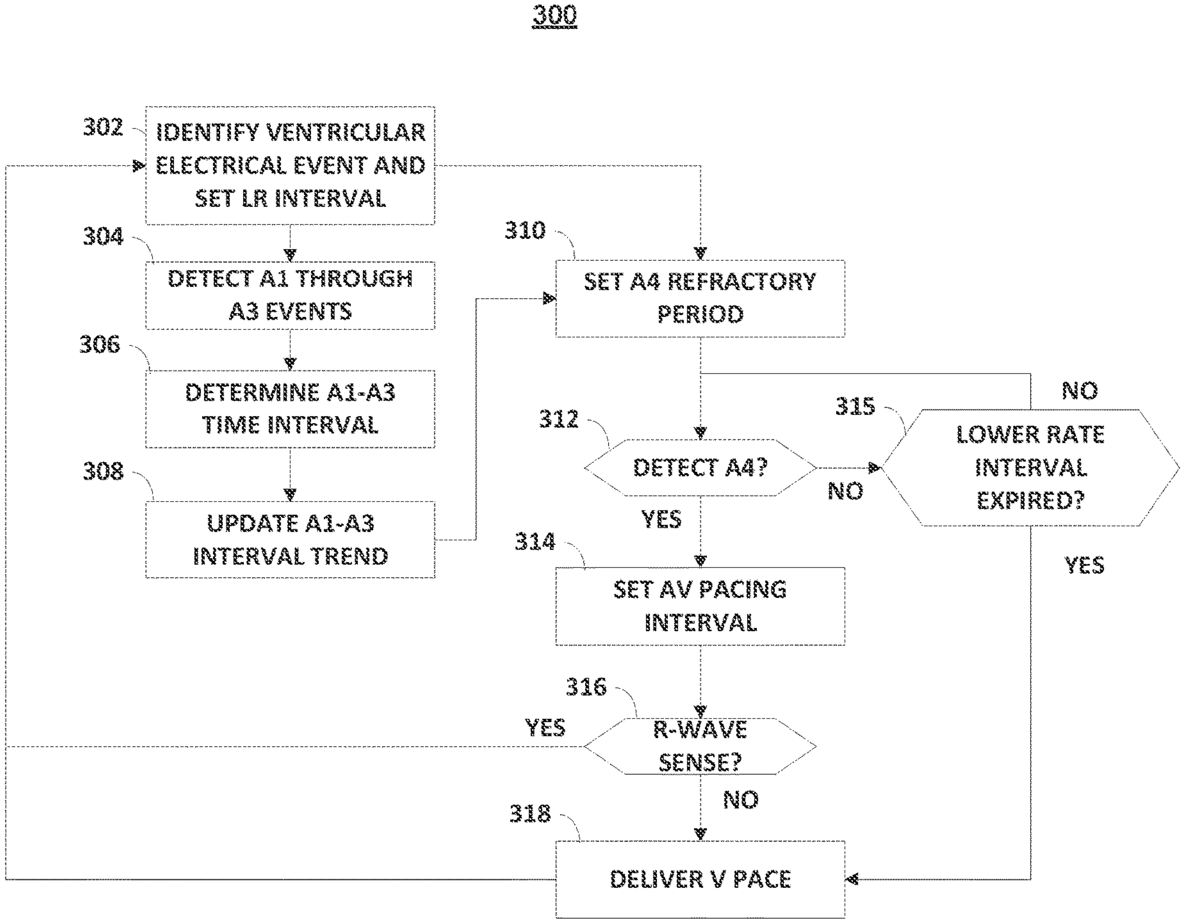
FIG. 5 is a flow chart of one method performed by an intracardiac ventricular pacemaker for detecting an atrial systolic event from a motion sensor signal and controlling ventricular pacing.

FIG. 5 is a flow chart 300 of one method performed by RV pacemaker 14 for detecting the A4 event and controlling ventricular pacing. At block 302, control circuit 206 identifies a ventricular electrical event. The ventricular event may be an R-wave sensed event signal received from sensing circuit 204 or a ventricular pacing pulse delivered by pulse generator 202. Since the ventricular A1, A2 and A3 events may have different characteristics during an intrinsic ventricular rhythm than during a ventricular paced rhythm, the methods described herein for determining amplitudes, time intervals or other characteristics of the A1, A2 and A3 events for use in setting A4 detection control parameters or confirming A4 event detection may be determined for both an intrinsic ventricular rhythm and a ventricular paced rhythm.

For example, as described in conjunction with the flow charts and timing diagrams presented herein, various time intervals, sensing windows, atrial refractory period, and atrial event detection threshold amplitude may be set based on characterizations of one or more of the A1, A2 and A3 events. One set of A4 detection control parameters and characteristics of the A1, A2 and A3 events may be determined and stored for use during episodes of ventricular sensing (ventricular intrinsic rhythm), and another set of A4 detection control parameters and characteristics of the A1, A2 and A3 events may be determined and stored for use during episodes of ventricular pacing.

During ventricular sensing, control circuit 206 may be configured to discriminate a normal sinus R-wave from a premature ventricular contraction (PVC) so that ventricular events identified at block 302 for use in starting a search for the A1 through A4 events from the motion sensor signal do not include PVCs. When a ventricular event, sensed or paced, is identified at block 302 that is not a PVC, pace timing circuit 242 may set an escape interval timer to a ventricular LR pacing interval. If the LR pacing interval expires (as described below in conjunction with block 315), a ventricular pacing pulse may be delivered, asynchronous to atrial activity, in order to maintain some minimum, base ventricular rate.

At block 304, atrial event detector 240 detects the A1 through A3 motion signals. Briefly, atrial event detector 240 may compare the motion sensor signal to one or more pre-determined detection threshold amplitudes during one or more time windows set in response to identifying the ventricular event at bock 302 for detecting the A1 through A3 events. In some examples, the A4 event may also be detected at block 304 to increase confidence in the positive identification of each of the four motion sensor signals A1 through A4 in a given cardiac cycle. In this example, the A1 through A3 events, and optionally A4, may be detected on a beat-by-beat basis.

After the A1 through A3 events are detected, the A1-A3 time interval is determined at block 304 as the time interval from the A1 event detection to the A3 event detection. The A1-A3 time interval may be used to update an A1-A3 interval trend at block 308. For example, a running average A1-A3 time interval may be updated at block 308 using the most recent N A1-A3 time interval measurements, e.g., the most recent three to twelve A1-A3 time intervals.

The A1-A3 time interval is used to set a post-ventricular atrial refractory period at block 310. This atrial refractory period is also referred to herein as an "A4 refractory period" because A4 event detection is inhibited during the atrial refractory period in some examples. When a ventricular electrical event is identified at block 302, atrial event detector 240 may start the atrial refractory period at block 310. The atrial refractory period may be set based on the A1-A3 time interval, e.g., to a percentage longer than or a fixed interval longer than the A1-A3 time interval. For example, the atrial refractory period may be set to be 50 to 150 ms longer than the A1-A3 time interval, though shorter or longer fixed intervals may be added to the A1-A3 time interval for setting the atrial refractory period. The fixed time interval used to set the atrial refractory period may vary depending on heart rate in some examples.

During the atrial refractory period, any motion sensor events that are detected, or cross a detection threshold amplitude, are ignored for the purposes of triggering a ventricular pacing pulse and starting an AV pacing interval. Ventricular mechanical events A1 through A3 may be detected during the atrial refractory period, as indicated at block 304, to determine the A1-A3 time interval and update the A1-A3 interval trend (blocks 306 and 308), either periodically or on a beat-by-beat basis.

At block 312, atrial event detector circuit 240 monitors the motion sensor signal to detect the A4 event after the expiration of the atrial refractory period. If the A4 event is not detected before the LR pacing interval expires (block 315), a ventricular pacing pulse is delivered at block 316 to ensure a minimum ventricular rate, e.g., at least 40 to 60 beats per minute. Furthermore, it is to be understood that if an intrinsic R-wave is sensed before an A4 event is detected, the process of FIG. 5 may return to block 302 where the sensed R-wave is identified as a ventricular electrical event, and control circuit 206 restarts the process of detecting the A4 event on the next ventricular cycle.

If the A4 event is detected before the LR pacing interval expires, control circuit 206 sets the AV pacing interval at block 314 in response to detecting the A4 event. If an intrinsic R-wave is not sensed from the cardiac electrical signal by sensing circuit 204 during the AV pacing interval, "no" branch of block 316, a ventricular pacing pulse is delivered by pulse generator 202 at block 318 upon expiration of the AV pacing interval. The ventricular pacing pulse, if delivered, and otherwise the sensed R-wave, is identified as the next ventricular event at block 302, and the process repeats.

In this way, the A1 through A3 events may be detected from the motion sensor signal on a beat-by-beat (or less frequent) basis for updating the A1-A3 time interval trend used to set the atrial refractory period to provide a high likelihood of positively detecting the A4 event and properly timing a ventricular pacing pulse in synchrony with the atrial event. Other motion sensor signal events A1 through A3 are unlikely to be falsely detected as the A4 event by applying the atrial refractory period set based on the A1-A3 timing.

In some examples, rather than determining an A1-A3 time interval, a time interval to the A2 event may be determined so that the atrial refractory period is set based on the A1-A2 time interval to extend through at least the A2 event and expire before the A3 event. In this example, an A4 detection threshold amplitude may be set higher than an expected A3 event amplitude to allow detection of the A4 event earlier in the ventricular cycle, for example as the atrial rate is increasing. In other cases, the time interval from the identified ventricular electrical event to the A1, A2 or A3 event may be determined and used in setting the atrial refractory period.

In some examples, the process of blocks 304 through 308 is performed periodically rather than on a beat-by-beat basis. For example detection of A1-A3 events during the atrial refractory period may occur on every third cardiac cycle, every eighth cardiac cycle, once a minute or other predetermined schedule for updating the A1-A3 time interval (or other ventricular event time interval as discussed above) used for setting the atrial refractory period at block 310. In some cases, the heart rate, paced or intrinsic, may be monitored and the A1-A3 events may be detected for updating the A1-A3 interval trend when the heart rate changes by more than a predetermined amount. For example, ventricular event intervals between consecutive ventricular events may be determined upon identifying ventricular events at block 302. The ventricular event intervals may be RR intervals between consecutively sensed intrinsic R-waves or VV intervals between consecutively delivered ventricular pacing pulses and may include RV intervals between a sensed intrinsic R-wave and a consecutively delivered pacing pulse and VR intervals between a delivered pacing pulse and a consecutively sensed R-wave. Both the intrinsic heart rate and the paced rate may change as the intrinsic ventricular rate varies and as the RV pacemaker 14 tracks an atrial rate. If the ventricular event interval changes or a trend in the ventricular event interval changes by more than a predetermined amount, the control circuit 206 may perform blocks 304 through 308 to update the A1-A3 interval trend used for setting the atrial refractory period.

In other examples, if the A4 event is not detected at block 312 after the atrial refractory period and before the next ventricular event (intrinsic or paced) is identified at block 302, the control circuit 206 may perform the process of blocks 304 through 306 for a predetermined number of consecutive or non-consecutive cardiac cycles to update the A1-A3 interval trend used to set the atrial refractory period to restore A4 detection.

Figure 6:
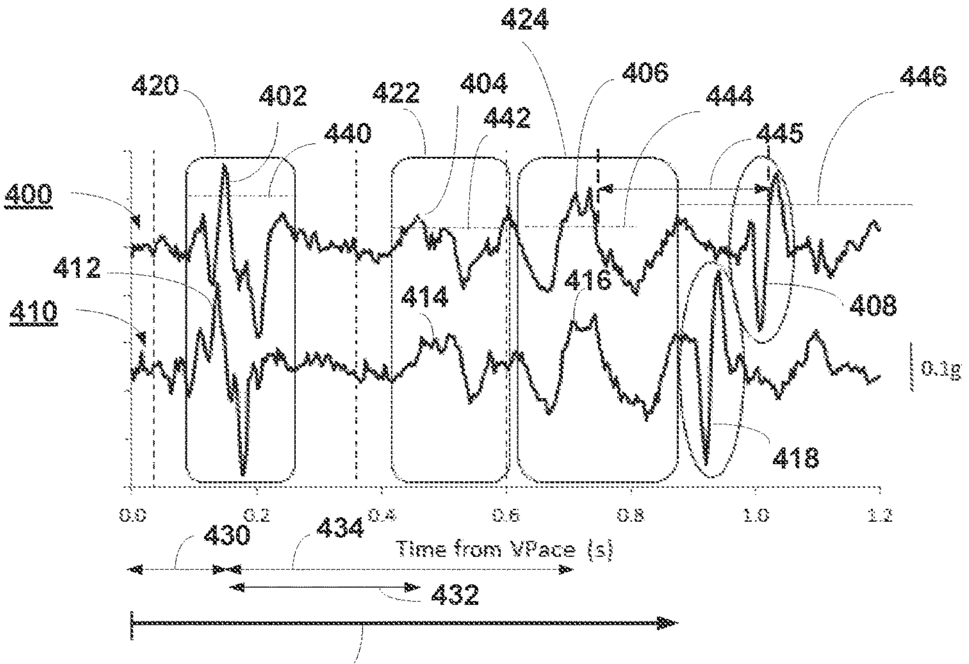
FIG. 6 is an example of a motion sensor signal acquired over two different ventricular cycles.

FIG. 6 is an example of a motion sensor signals 400 and 410 acquired over two different cardiac cycles. A ventricular pacing pulse is delivered at time 0.0 seconds for both cardiac cycles. The top sensor signal 400 is received over one cardiac cycle and the bottom sensor signal 401 is received over a different cardiac cycle. The two signals 400 and 410 are aligned in time at 0.0 seconds, the time of the ventricular pacing pulse delivery.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (occurring with ventricular isovolumic relaxation) and the A3 events 406 and 416 (occurring during passive ventricular filling) are well-aligned in time. Since the A1, A2 and A3 events are ventricular events, occurring during ventricular contraction, ventricular relaxation, and passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave, however, during a stable paced or intrinsic ventricular rhythm, the relative timing of A1, A2 and A3 events to each other and the immediately preceding ventricular electrical event is expected to be consistent for a given heart rate.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining the atrial refractory period and increasing confidence in reliably detecting A4 events 408 and 418. In some examples, an A1 sensing window 420 may be set based on an expected Vpace-A1 time interval. The Vpace-A1 time interval 430 may be measured when the motion sensor signal 400 or 410 crosses an A1 sensing threshold amplitude 440. The A1 sensing window 420 may be adjusted on the next cardiac cycle based on the Vpace-A1 time interval 430 determined on the current cardiac cycle or a running average Vpace-A1 time interval.

An A2 sensing window 422 may be set based on an expected Vpace-A2 time interval (not explicitly shown but understood to be the total time from 0.0 seconds to an A2 event detection) or an A1-A2 time interval 432 (time from A1 detection to time of A2 detection). The A2 event 404 or

414 may be detected at the time of the first positive-going crossing of an A2 sensing threshold amplitude 442 by the motion sensor signal 400 or 410 during the A2 sensing window 422. The A2 sensing window 422 may be adjusted on the next cardiac cycle based on the Vpace-A2 time interval or A1-A2 time interval 432 determined on the current cardiac cycle.

Similarly, an A3 sensing window 424 may be set based on an expected Vpace-A3 time interval (not explicitly labeled but understood to be sum of time intervals 430 and 434), A1-A3 time interval 434, or A2-A3 time interval (not explicitly labeled but understood to be the time interval from the sensed A2 event 404 or 414 to the sensed A3 event 406 or 416). The A3 event 406 or 416 may be detected during the A3 sensing window 424 when the motion sensor signal 400 or 410, respectively, crosses an A3 sensing threshold amplitude 444. The A3 sensing window 424 may be adjusted on the next cardiac cycle based on the Vpace-A3 time interval, A1-A3 time interval 434, or the A2-A3 time interval determined during the current cardiac cycle.

Each of the sensing windows 420, 422 and 424 may be set based on a history of time intervals determined from a ventricular pacing pulse or sensed intrinsic R-wave to the respective A1 event 402 or 412, A2 event 404 or 414 and A3 event 406 or 416 or based on a history of time intervals between the detected A1, A2 and A3 events or any combination thereof. For example, the A2 sensing window 422 may be set to start based on time intervals measured between a ventricular pacing pulse or sensed R-wave and the detected A1 event. The end of the A2 sensing window 422 may be set to start based on an A1-A2 time interval 432 or based on an A1-A3 time interval 434. It is recognized that numerous methods may be conceived for setting the A1, A2 and A3 sensing windows 420, 422 and 424, respectively, based on the consistency of the expected time intervals between any combinations of the ventricular electrical event (paced or sensed) and subsequent A1, A2 and A3 events. Furthermore, it is contemplated that these sensing windows 420, 422 and 424 may be set according to different control parameters, such as different fixed time intervals added to or subtracted from measured event time intervals depending on whether the ventricular electrical event is a paced or sensed event and/or depending on heart rate. The event time intervals that may be measured and used for setting the onset, offset and duration of the sensing windows 420, 422 and 424 may include any one or combination of the Vpace-A1, Vpace-A2, Vpace-A3, Rsense-A1, Rsense-A2, Rsense-A3, A1-A2, A1-A3, and/or A2-A3 time intervals determined during a paced and/or intrinsic rhythm.

The sensing threshold amplitudes 440, 442 and 444 may be set uniquely during each of the respective sensing windows 420, 422 and 424 or set to a fixed, common value for all sensing windows. The sensing threshold amplitudes 440, 442, and 444 may be fixed or decaying thresholds and may be automatically adjusted thresholds set to starting threshold values based on the peak motion sensor signal amplitude detected during each respective window 420, 422 and 424. The motion sensor signals 400 and 410 are shown as raw signals, but the motion sensor signal may be filtered, amplified and rectified by circuitry included in motion sensor 212 to provide control circuit 206 with a rectified signal that is used to detect the A1 through A4 events.

A post-ventricular, atrial refractory period 436 may be set based on the A1-A3 time interval 434 or based on the Vpace-A3 time interval (sum of Vpace-A1 interval 430 and A1-A3 time interval 434). In some examples, the atrial refractory period 436 ends upon the expiration of the A3 sensing window 424. In other examples, the atrial refractory period 436 ends after the expiration of the A3 sensing window 424. The A4 event 408 or 418 may be detected in response to a crossing of an A4 sensing threshold amplitude 446, e.g., the first positive-going crossing or a last negative-going crossing, by the rectified motion sensor signal.

In some examples, the A4 detection is confirmed when the A1, A2 and A3 events have each been detected during the atrial refractory period 436. If any one of the A1, A2 or A3 events was not detected during the atrial refractory period 436, the A4 event detection based on a crossing of threshold 446 may not be confirmed and not used for starting an AV pacing interval. In other examples, at least one of the A1, A2 or A3 events may be required to be detected during a respective sensing window 420, 422, or 424 on a beat-by-beat basis for confirming an A4 detection after the atrial refractory period 436.

The A1, A2 and/or A3 events sensed during the respective A1 sensing window 420, A2 sensing window 422 and A3 sensing window 424 may be used for updating the atrial refractory period 436 as described in conjunction with FIG. 5 on a beat-by-beat or less frequent basis without requiring positive detection of each of A1, A2, and/or A3 for confirming an A4 detection on each beat. Setting the atrial refractory period based on detection and relative timing of the A1 through A3 events enables the atrial refractory period to be set based on the consistent timing of the ventricular motion sensor signal events so that A4 events may be detected with high reliability even when the timing of the A4 event relative to the A1-A3 events and the preceding ventricular electrical event is variable.

In some examples, an A3-A4 event interval 445 is determined and used for adjusting the A4 refractory period 436. For example, the A3 event 406 may be detected by detecting the last, negative-going crossing of an A3 event detection threshold amplitude 444 during the A3 sensing window 424. The A4 event 408 may be detected by the first positive-going crossing of the A4 event detection threshold amplitude 446 after the expiration of the A4 refractory period 436. The A3-A4 event interval 445 is determined as the time from the A3 event detection and the time of the A4 event detection. This A3-A4 event time may be compared to a previous A3-A4 event time, e.g., compared to one or more preceding A3-A4 event times which may be determined during the respective one or more preceding cardiac cycles or to a running average A3-A4 event time determined from two to five or other predetermined number of previously determined A3-A4 event times. If a change in the A3-A4 event time interval compared to one or more preceding A3-A4 event times is detected, the A4 refractory period 436 may be adjusted. As the A3-A4 event time is detected to shorten or increase, the control circuit 206 may decrease or lengthen the A4 refractory period 436, respectively, to account for changes in the time interval 445 between the ventricular diastolic event and the atrial systolic event as the atrial rate changes.

Figure 7:
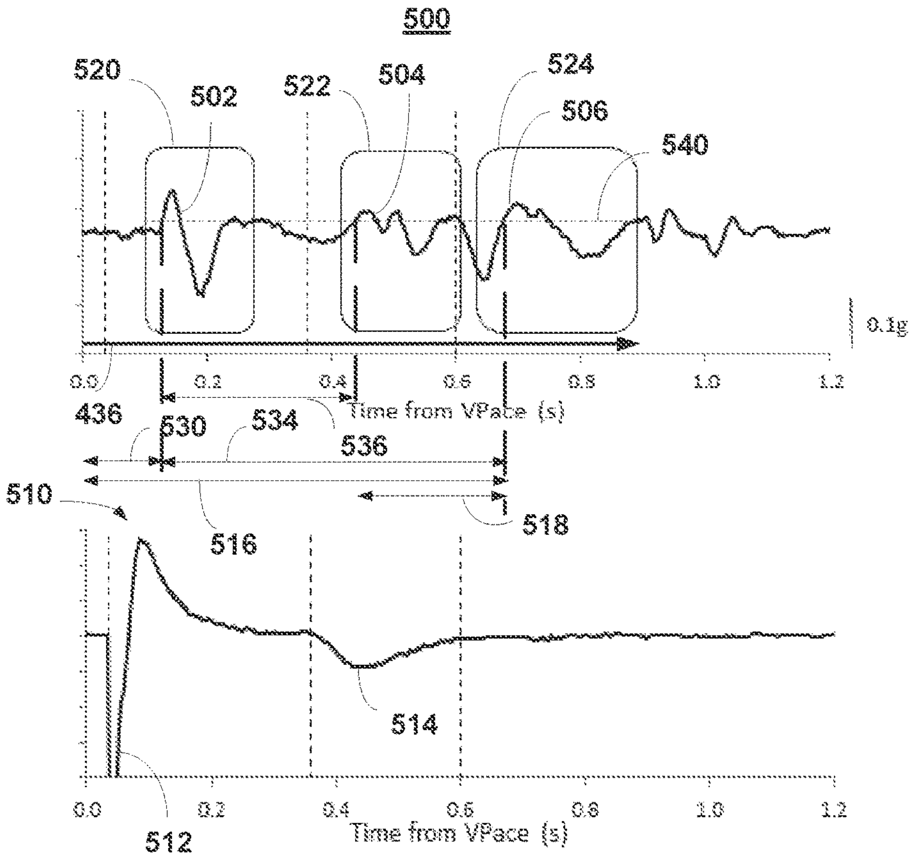
FIG. 7 is an averaged motion sensor signal.

FIG. 7 is an averaged motion sensor signal 500 that may be determined by control circuit 206 by averaging the motion sensor signal acquired over multiple cardiac cycles, e.g., signals 400 and 410 of FIG. 6. The averaged motion sensor signal 500 may represent the average of 3 to 20 or other predetermined number of cardiac cycles. The raw motion sensor signal or a filtered, amplified and/or rectified motion sensor signal may be buffered beginning from a ventricular electrical event, pacing pulse or sensed R-wave, at time 0.0 seconds until the next ventricular electrical event. The buffered motion sensor signal obtained over one cardiac cycle may be averaged with the buffered motion sensor signals obtained over a predetermined number of other cardiac cycles to produce averaged motion sensor signal 500.

A ventricular electrical signal 510 is shown aligned in time with averaged motion sensor signal 500. Ventricular electrical signal 510 may be passed from sensing circuit 204 to control circuit 206 and includes an R-wave 512, which may be an evoked or intrinsic R-wave, and a T-wave 514. R-wave 512 is followed by the ventricular contraction A1 event 502. The ventricular relaxation A2 event 504 occurs during T-wave 514. The passive ventricular filling A3 event 506 occurs after T-wave 514.

Since the A1, A2 and A3 events are ventricular mechanical events, they occur at consistent time intervals relative to each other and relative to ventricular electrical events (R-wave 512 and T-wave 514). As a result, the signal-to-noise ratio of the A1 signal 502, A2 signal 504 and A3 signal 506 is improved in the averaged motion sensor signal 500 compared to the single-cycle motion sensor signals 400 and 410 of FIG. 6. The averaged A1 event 502, A2 event 504 and A3 event 506 have an improved signal-to-noise ratio, making A1, A2, and A3 event detection from the averaged motion signal 500 more reliable.

A single event detection threshold amplitude 540 may be defined such that the first positive-going crossing of the threshold 540 by the averaged, rectified motion sensor signal 500 within the A1 sensing window 520, within the A2 sensing window 522 and within the A3 sensing window 524 is detected as the respective A1 event 502, A2 event 504, and A3 event 506. The threshold crossing may be a first, positive-going crossing or a last, negative-going crossing in various examples. Alternatively, unique detection threshold amplitudes may be defined for each sensing window 520, 522 and 524 for detecting the respective A1, A2 and A3 events. The sensing windows 520, 522 and 524 may be initially set according to expected A1, A2 and A3 event timing following the ventricular pacing pulse or R-wave 512 and may be adjusted according to the actual detection time of each respective A1 event 502, A2 event 504, and A3 event 506 based on a threshold crossing. The sensing windows 520, 522 and 524 may be set based on ventricular pacing rate or atrial event rate, e.g., based on A4-A4 event intervals. The sensing windows 520, 522 and 524 may also be set differently following a ventricular pacing pulse than following an intrinsic R-wave sensed event since the timing of the A1, A2 and A3 events and T-wave 514 may be altered during ventricular pacing compared to during an intrinsic ventricular rhythm.

The atrial systolic A4 event timing, which is independent of the ventricular electrical event timing, may be more variable from one cardiac cycle to the next with respect to the ventricular electrical and mechanical events, e.g., as shown by the relative timing of the A4 events 408 and 418 of signals 400 and 410 (FIG. 6). As a result, the A4 signal is largely attenuated in the averaged motion signal 500 in FIG. 7. The improved signal-to-noise ratio of the A1 through A3 events and attenuation of the A4 event in the averaged motion signal 500 enables control circuit 206 to reliably detect the signal averaged A1 event 502, A2 event 504 and A3 event 506 for determining one or more ventricular event time intervals for use in setting A1, A2 and A3 detection windows 420, 422, and 424, respectively, setting detection threshold amplitudes for detecting the A1, A2, A3 and/or A4 events, and/or setting atrial refractory period 436 used on a beat-by-beat basis for A4 event detection as shown in FIG. 6.

For example, a ventricular R-wave or pacing pulse to A1 time interval 530, an A1-A3 time interval 534, A1-A2 time interval 536, a ventricular R-wave or pacing pulse to A3 time interval 516, and/or a T-wave to A3 time interval 518 or any combination thereof may be determined by control circuit 206 from the averaged motion signal 500 and the cardiac electrical signal 510. The atrial refractory period 436 is started upon delivering a ventricular pacing pulse or sensing an intrinsic R-wave. The atrial refractory period 436 may be set to expire after a predetermined time interval, e.g., 30 to 100 ms, after the A3 time interval 516. For instance, if time interval 516 is 700 ms, the atrial refractory period 436 may be set to expire 750 ms after the ventricular pacing pulse or sensed R-wave that started the atrial refractory period. Instead of using a time interval ending with the A3 event detection, a time interval ending with the A2 event detection may be determined and used in controlling the duration of the atrial refractory period 436. As described above, the A2 event, which occurs during T-wave 514, is an indicator of the end of ventricular mechanical systole and the onset of ventricular mechanical diastole. The A3 event occurs during ventricular mechanical diastole, during the passive ventricular filling phase. As such the timing of the A2 event 504 or the timing of the A3 event 506 relative to another ventricular electrical event (ventricular pacing pulse, R-wave 512, or T-wave 514) may be used for controlling the duration and expiration time of atrial refractory period 436. In other words, the timing of a ventricular mechanical diastolic event, A2 event 504 or A3 event 506, may be determined and used to set the atrial refractory period 436 that is applied on a beat-by-beat basis for detecting A4 events.

The T-wave 514 may be sensed by sensing circuit 206 on a beat-by-beat basis by control circuit 206 or by sensing circuit 204 from cardiac electrical signal 510. The T-wave 514 may be sensed at a maximum peak amplitude of a rectified cardiac electrical signal or a maximum absolute peak amplitude in a non-rectified cardiac signal received by control circuit 206 from sensing circuit 204. Alternatively, T-wave 514 may be sensed by sensing circuit 204 in response to the cardiac electrical signal crossing a T-wave sensing threshold amplitude after the ventricular pacing pulse or R-wave sensed event signal. In some cases, a T-wave sensing window may be applied after the R-wave sensed event signal or a delivered pacing pulse to facilitate T-wave sensing.

The T-wave 514 may be sensed during the atrial refractory period 436. Control circuit 206 may terminate the atrial refractory period 436 at a predetermined time interval after sensing T-wave 514. For instance if the T-wave to A3 time interval 518 is determined to be 150 ms from the averaged motion signal 500, control circuit 206 may terminate the atrial refractory period 436 at 180 ms after sensing the T-wave to promote reliable sensing of the A4 event.

Atrial event detector circuit 240 may be a processor-based circuit that determines the averaged motion sensor signal 500 over multiple cardiac cycles, detects A1, A2 and A3 events 502, 504, and 506 from the averaged motion sensor signal 500, and sets the atrial refractory period 436 based on the timing of at least one ventricular mechanical diastolic event, e.g., the A3 event 506, detected from the average motion sensor signal 500. In other examples, the A2 event is used as a ventricular diastolic mechanical event for marking the approximate timing of the onset of ventricular diastole. The A4 event, e.g., event 408 or 418 (FIG. 6) may be detected on a beat-by-beat basis from the non-averaged motion sensor signal after the atrial refractory period 436 expires.

Figure 8:
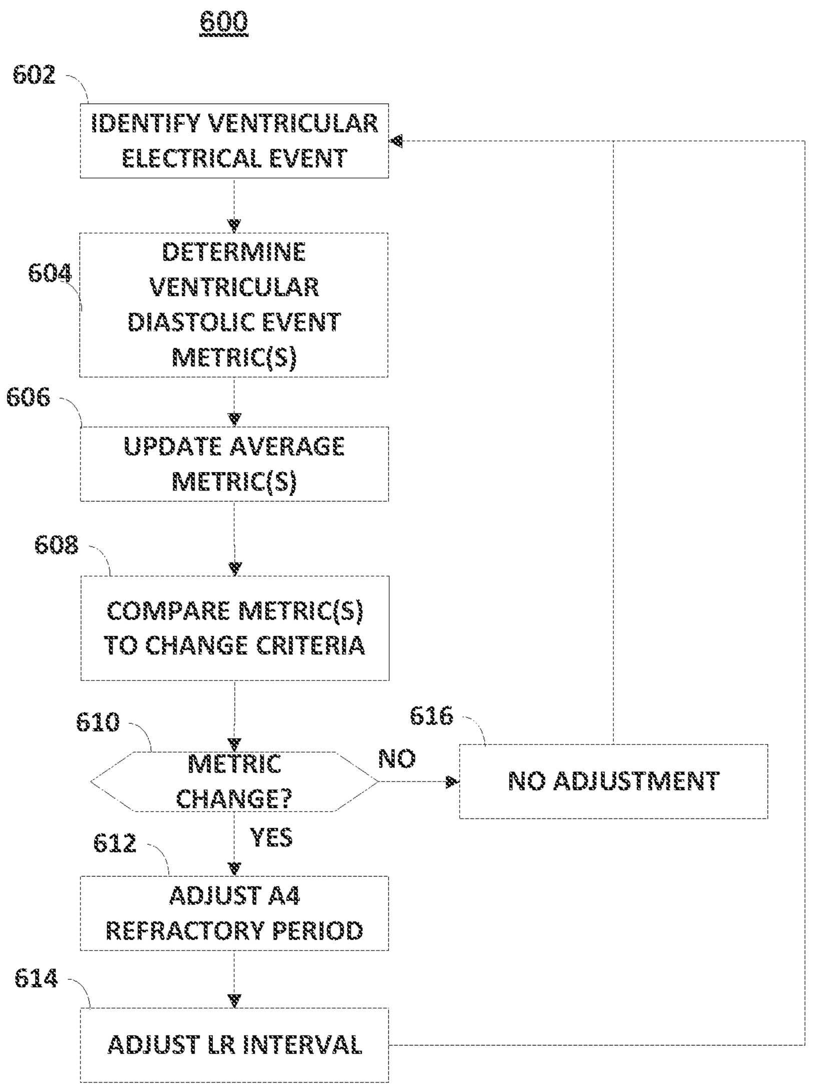
FIG. 8 is a flow chart of a method performed by an intracardiac ventricular pacemaker for controlling an atrial refractory period.

FIG. 8 is a flow chart 600 of a method performed by RV pacemaker 14 for controlling the A4 refractory period. The time interval from a ventricular systolic event (electrical or mechanical) to a subsequent ventricular diastolic mechanical event is expected to shorten when the intrinsic heart rate is about to or is increasing. Tracking a change in a time interval expiring on a ventricular diastolic mechanical event, e.g., ending on the A2 event or the A3 event, allows the A4 refractory period to be adjusted to maintain reliable sensing of the A4 events across heart rate changes.

The process of flow chart 600 may be performed on a periodic basis, on a beat-by-beat basis, or triggered in response to a change in the rate of A4 events, triggered in response to a loss of A4 event detections, triggered in response to detecting an increase in patient activity, triggered in response to detecting a change in patient posture, or in response to another indicator of a possible change in heart rate. The process of flow chart 600 may also be performed upon pacing mode switching, e.g., from a non-atrial tracking pacing mode such as VVI or VDI to an atrial tracking pacing mode such as VDD, and/or may be performed periodically when pacing in a non-atrial tracking mode, such as a VVI(R) pacing mode, for use in adjusting a ventricular LR pacing interval.

At block 602, a ventricular electrical event is identified, which may be a sensed intrinsic R-wave or delivered ventricular pacing pulse. One or more ventricular diastolic event metrics are determined at block 604. In various examples, A2 event metrics and/or A3 event metrics are determined at block 604. For example, one ventricular diastolic event metric determined at block 604 may be an A3-A4 time interval, e.g., A3-A4 time interval 445 shown in FIG. 6. In other examples, the ventricular diastolic event metric(s) is/are determined as A2 event metrics. It is to be understood that one or more ventricular diastolic event metrics may be determined at block 604 as one or more A2 event metrics, one or more A3 event metrics, or any combination of one or more A2 event metrics and one or more A3 event metrics. A diastolic event metric may be a time intervals beginning or ending on the A2 event or A3 event, an event amplitude, or other event feature.

Since the ventricular diastolic events may occur at a different time during paced ventricular cycles than during intrinsic ventricular cycles, and/or have a different amplitude or morphology, the process of flow chart 600 may be performed during a stable, intrinsic heart rhythm for establishing ventricular diastolic event metrics of an intrinsic rhythm and during a paced ventricular rhythm to establish a second set of ventricular diastolic event metrics of a paced rhythm.

In one example, at least an A2 event time interval is determined at block 604 as a ventricular diastolic event metric. The A2 event time interval may be determined as the time interval from an intrinsic sensed R-wave to an A2 event detection, a ventricular pacing pulse to an A2 event detection, or an A1 event detection to an A2 event detection. In other examples, one or more other A2 event metrics may be determined such as an A2 event amplitude. At block 606, the A2 metric(s) determined at block 604 for the current ventricular cycle are used to update an average A2 metric. For example, an A2 event metric may be determined as the A2 event time interval, which is used to update a running average of a predetermined number of A2 event time intervals, e.g., a running average of three to twenty event time intervals, at block 606.

As described below, the ventricular diastolic event metric(s) are used for adjusting the A4 refractory period and/or the ventricular LR pacing interval. In some examples, an average metric determined at block 606 is stored for the current heart rate, which may be determined based on detected A4 event time intervals. An average A2 metric may be stored for each one of multiple heart rates or heart rate ranges as A2 event metric data is accumulated so that the average A2 event metric(s) are available for use in making adjustments to the A4 refractory period and/or the LR pacing interval as the atrial rate changes (e.g., as determined from A4 event intervals) without having to repeat the determination of average A2 metrics.

At block 608, the ventricular diastolic event metric is compared to change criteria for detecting a change in the ventricular diastolic event metric compared to at least one previously determined ventricular diastolic event metric. For example, an updated averaged A2 metric(s) may be compared to change criteria at block 608 for detecting an impending change in heart rate. In some cases, the currently determined most recent A2 metric is compared to the updated average A2 metric to determine if a threshold change in the A2 metric has occurred. In other examples, the average A2 metric may be compared to a previous average A2 metric or to a predetermined threshold to determine if a change in the A2 metric has occurred indicative of an imminent or needed change in heart rate. For example, the A2 event time interval may decrease by 10% or other threshold change as a predictive indicator that the heart rate is going to increase, or needs to increase in response to an increased patient metabolic demand. As a result the A4 event is expected to shift earlier in the ventricular cycle warranting an adjustment to the A4 refractory period.

If the control circuit 206 determines that change criteria are not satisfied, an A2 metric change is not detected at block 610, and no adjustment is made to the A4 refractory period or any other A4 event detection control parameters. If the change criteria are met at block 608, an A2 metric change is detected at block 610, and the control circuit 206 adjusts the A4 refractory period at block 612. If the A2 event time interval has decreased, the A4 refractory period is decreased; if the A2 event time interval has increased, the A4 refractory period is increased.

In this example, the A4 refractory period may initially be set based on an A3 time interval as described above in conjunction with FIG. 5. The A3 time interval may be determined on a beat-by-beat basis or from an averaged motion sensor signal, e.g., as described in conjunction with FIG. 7. The A4 refractory period initially set based on the A3 time interval is adjusted based on changes in the A2 event metric, used as an indicator of an expected change in heart rate, which may move the A4 event earlier or later in the ventricular cycle. Adjustments to the A4 refractory period may be performed by control module 206 by increasing or decreasing the A4 refractory period from a current value to an adjusted value by increasing or decreasing the A4 refractory period by one or more predetermined step changes. The size of the step change may be based on the amount of change detected in the A2 metric. For example, if the A2 event time interval changes by up to 15% compared to at least one preceding A2 event time interval or compared to the updated average A2 event time interval, the A4 refractory period may be adjusted by 10 ms. If the A2 event time interval changes by 15 to 30% compared to at least one preceding A2 event time interval or compared to the updated average A2 event time interval, the A4 refractory period may be adjusted by 20 ms. These examples are illustrative in nature, and it is understood that the amount of change in the A2 event metric and corresponding size of the adjustment to the A4 refractory period may be based on clinical and/or individual patient data.

In some examples, control circuit 206 adjusts the lower rate (LR) pacing interval at block 614, which may be a temporary LR pacing interval that is shorter than a minimum or base pacing rate interval, in response to detecting the A2 metric change. A permanent LR pacing interval may be programmed and stored in memory 210 corresponding to a permanent lower pacing rate which is the minimum or base pacing rate, e.g., 40 to 60 pulses per minute. The LR pacing interval may be adjusted from the permanent LR pacing interval to a temporary pacing interval based on a sensor indicated pacing rate determined from a patient physical activity metric, which may also be determined from the motion sensor signal. The permanent or a temporary SIR-based LR pacing interval may be adjusted based on a change in the A2 metric.

For example, if the A2 event time interval decreases, it is anticipated that the patient's intrinsic heart rate is expected to rise. As such, the LR pacing interval set at block 302 of FIG. 5 may be shortened to provide a faster ventricular pacing rate in the absence of A4 event detection. The paced or sensed atrial rate may increase to meet an increased patient metabolic demand. If A4 events are not detected for tracking an accelerating atrial rate, a decrease in the A2 event time interval is used as an indication for a need for a higher heart rate. As such, the LR pacing interval is decreased at block 614 to provide a faster pacing rate. If the A2 event time interval increases, the LR pacing interval may be increased at block 614 based on the change in the A2 event metric. The LR pacing interval may be adjusted based on one, two or more average A2 metrics stored for different heart rates in some examples so that the LR pacing interval matches the heart rate that is stored with the corresponding average A2 metric value.

In some instances, therefore, the A4 refractory period and the LR pacing interval may be increased and decreased together as changes in the A2 metric are detected. In other examples, the adjustments to the LR pacing interval may be made less frequently by requiring a higher threshold change in the A2 metric before the LR pacing interval is adjusted than the threshold change required to adjust the A4 refractory period in response to an A2 metric change.

Changes to the A4 refractory period and LR interval in the method of flow chart 600 have been described based on detecting changes in an A2 event time interval as an indicator of an imminent change in heart rate. It is contemplated that an A3 event time interval may be used in addition to or instead of an A2 event time interval for detecting an expected change in heart rate and adjusting the A4 refractory period and/or LR pacing interval in response to the detected change.

Figure 9:
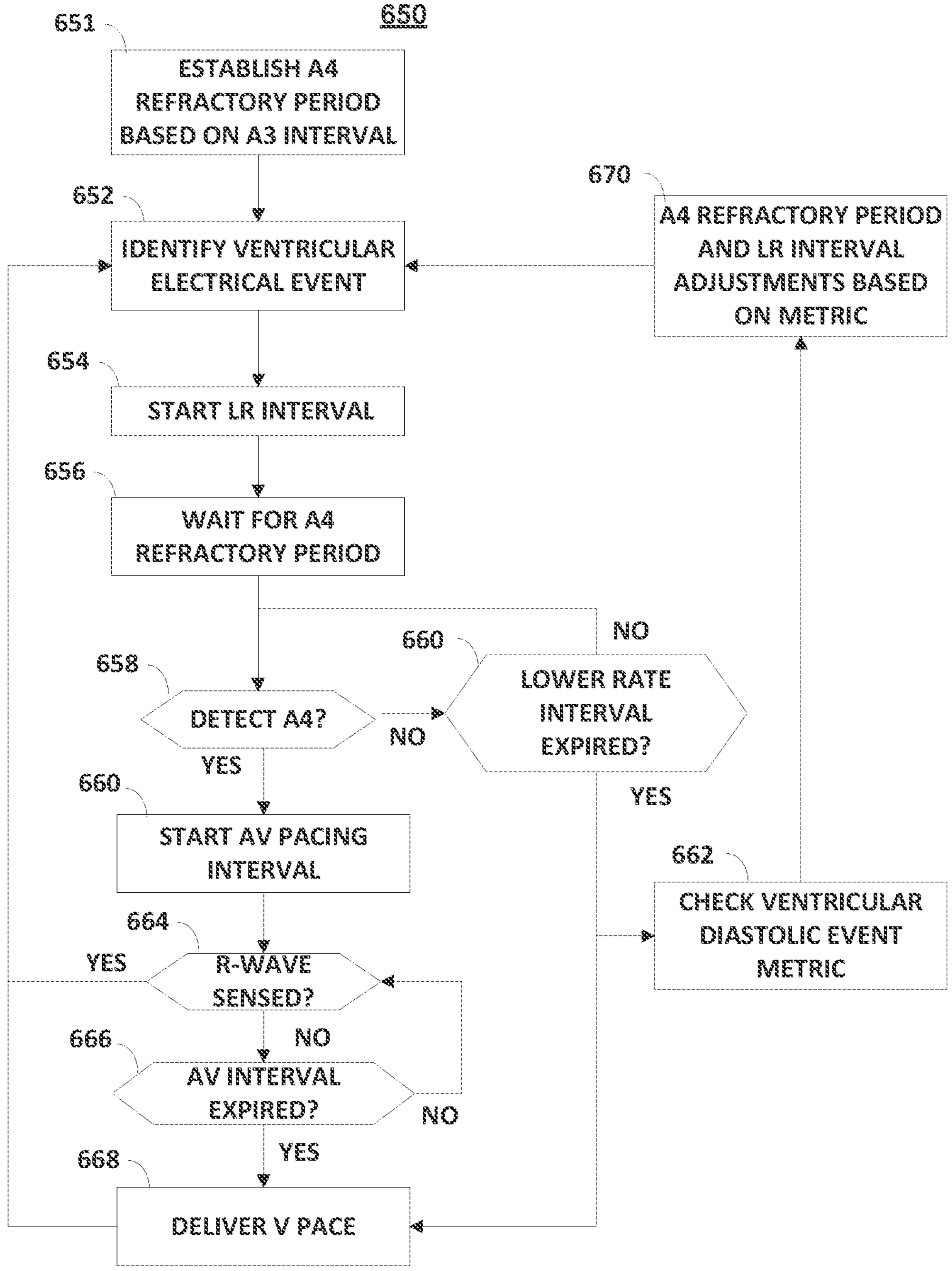
FIG. 9 is a flow chart of a method for controlling ventricular pacing by an intracardiac ventricular pacemaker according to another example.

FIG. 9 is a flow chart 650 of a method for controlling ventricular pacing by RV pacemaker 14 according to another example. At block 651, the A4 refractory period is initially established based on measurements of an A3 interval, e.g., an A1-A3 interval or a ventricular electrical event to an A3 interval, as described in conjunction with FIG. 5. The A4 refractory period may be set to a time interval that is expected to expire after an expected A3 event time. In some examples, the A4 refractory period may be set to a time interval that is expected to expire before the A3 event time but after the A2 event time in which case an adjustable, decaying or multi-level A4 event detection threshold amplitude may be used for detecting high amplitude A4 events that have become fused with the A3 event. Techniques disclosed herein for adjusting the A4 refractory period may be combined with techniques for setting an A4 refractory period and detecting A4 events that may become fused with the A3 event as generally disclosed in U.S. patent application Ser. No. 15/280,339, filed Sep. 29, 2016 and granted as U.S. Pat. No. 10,449,366 (Splett, et al.), incorporated herein by reference in its entirety.

At block 652, a ventricular electrical event, paced or sensed, is identified by control circuit 206. Control circuit 206 starts the ventricular LR pacing interval at block 654 and starts the A4 refractory period at block 656. After expiration of the A4 refractory period, the control circuit 206 waits for an A4 event to be detected at block 658, for example based on an A4 detection threshold amplitude crossing by the motion sensor signal. If the A4 event is detected, "yes" branch of block 658, the pace timing circuit 242 starts the AV pacing interval at block 660.

If an intrinsic R-wave is sensed by sensing circuit 204 (block 664), before the AV pacing interval expires, the process returns to block 652 and identifies the sensed R-wave as the next ventricular electrical event. If the AV pacing interval expires at block 666 without an R-wave sensed event signal produced by the sensing circuit 204, the scheduled ventricular pacing pulse is delivered at block 668. The ventricular pacing pulse is identified as the next ventricular electrical event at block 652 and the process repeats.

In some instances, the LR pacing interval started at block 654 may expire before an A4 event is detected. An A4 event may go undetected if it occurs during the A4 refractory period due to an increase in the intrinsic atrial rate or if it occurs later than the expiration of the LR pacing interval due to a decrease in the intrinsic atrial rate when the ventricular LR pacing interval has been shortened, e.g., to support rate responsive pacing. If the LR pacing interval expires without an A4 event detection ("yes" branch of block 660), a ventricular pacing pulse is delivered at block 668 and a ventricular mechanical diastolic event metric is checked at block 662 in response to the A4 event being undetected.

The ventricular mechanical diastolic event metric may be the A2 event time interval, the A3 event time interval, the amplitude of the A2 event or another metric of the A2 event, the A3 event, or any combination of A2 and/or A3 event metrics. The event metric may be checked using the techniques described in conjunction with FIG. 8. For example, a running average A2 event time interval may be updated on a beat-by-beat basis in parallel to the operations of flow chart 650 and compared to a current A2 event time interval determined from the current ventricular cycle or from the next ventricular cycle. If the A2 event time interval has changed, the A4 refractory period and/or the LR interval may be adjusted based on the A2 event time interval change at block 670. The A4 refractory period and the LR pacing interval may be shortened in response to the A2 interval decreasing or increased in response to the A2 interval increasing. The adjustment to the A4 refractory period and/or LR pacing interval may be proportional to the detected change in the A2 event time interval. The adjusted A4 refractory period and/or adjusted LR pacing interval are started at blocks 654 and 656, respectively, in response to the pacing pulse delivered at block 668, which is identified as the next ventricular electrical event (block 652).

In this way, if the LR pacing interval is causing ventricular pacing in advance of the A4 event during a slowing atrial rate, the LR pacing interval is increased to allow more time for detecting the A4 event. The A4 refractory period may be increased appropriately based on the A2 event time interval change. If an increase in atrial rate has occurred, A4 event detection is promoted by shortening the A4 refractory period to allow earlier detection of the A4 event. A shortened LR pacing interval provides ventricular pacing at a faster rate even when the A4 event is under-detected to support an increased metabolic demand as evidenced by the shortened A2 event time interval.

Figure 10:
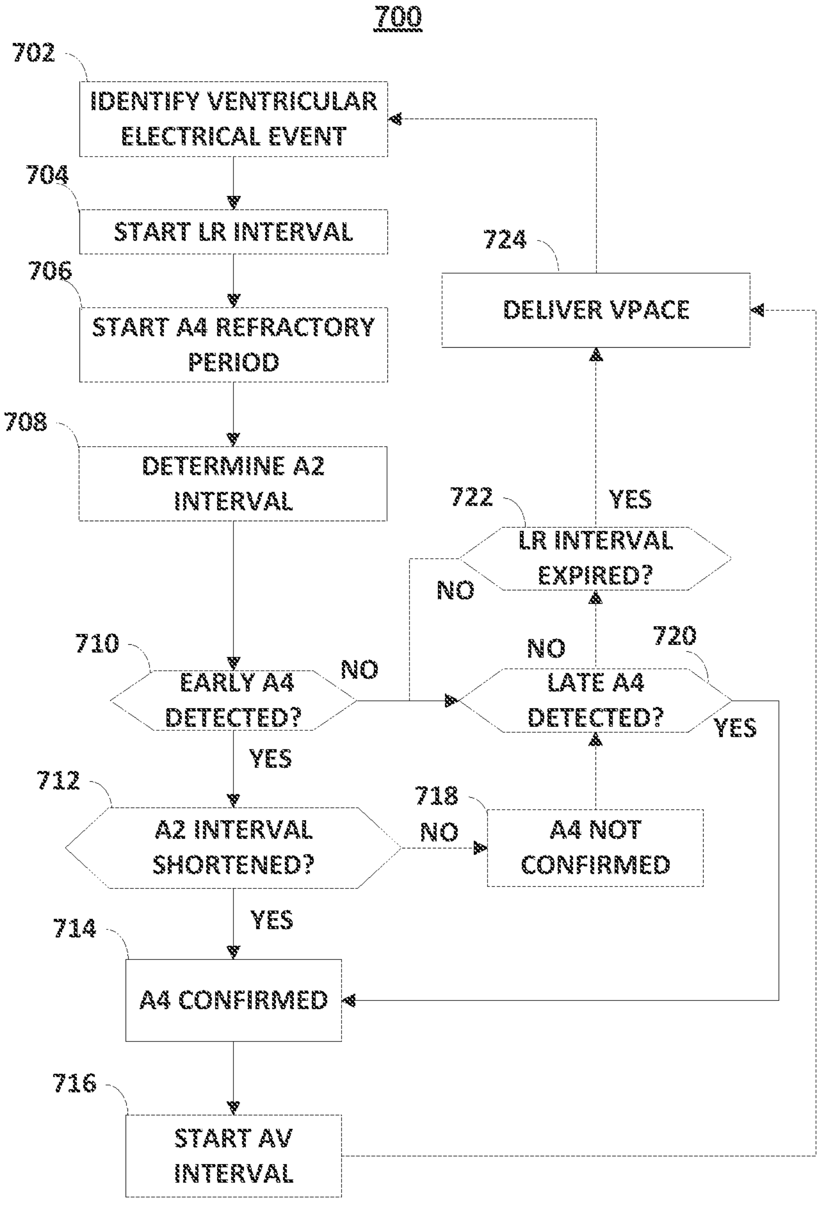
FIG. 10 is a flow chart of a method for monitoring for atrial mechanical systolic events by an intracardiac ventricular pacemaker according to another example.

FIG. 10 is a flow chart 700 of a method for monitoring for A4 events by RV pacemaker 14 according to another example. At block 702, a ventricular electrical event, paced or sensed, is identified. The LR pacing interval and the A4 refractory period are started at blocks 704 and 706 respectively. In this example, the A4 refractory period may be set to expire after an expected A2 event time and before, at or after the expected time of the A3 event. As the atrial rate increases, the A4 event may arrive earlier in the ventricular cycle, close in time to the A3 event or even concomitant with the A3 event causing a fused A3/A4 event signal. In order to maintain A4 event detection, the A4 refractory period may be set to a relatively short time period to enable detection of relatively early A4 events.

The A2 event time interval is determined at block 708 by control circuit 206 by detecting the A2 event from the motion sensor signal during the A4 refractory period and determining the time since the ventricular electrical event until the A2 event detection. In other examples, the A1 event may be detected, and an A1-A2 event time interval may be determined at block 708.

At block 710, control circuit 206 determines if an A4 event is detected early after the A4 refractory period. For instance if the A4 event is detected within a predetermined time window of the expiration of the A4 refractory period, the A4 event is detected as an early A4 event. The predetermined time window may be an A3 event time window defining a window of time that the A3 event is expected to occur. In other examples, a suspected A4 event may be detected during the A4 refractory period if the motion sensor signal crosses an A4 event detection threshold amplitude. This suspected A4 event may be preliminarily detected as an early A4 event if the detection threshold amplitude is crossed during the A4 refractory period.

If an early A4 event is detected based on early A4 event detection criteria, control circuit 206 determines if the A2 event time interval has shortened at block 712. The A2 event time interval determined at block 708 may be compared to the most recent preceding A2 event time interval, to a predetermined number of preceding A2 event time intervals, to a running average A2 event time interval, or to a predetermined threshold to detect A2 event time interval shortening at block 712.

If the A2 event time interval has shortened based on the criteria applied at block 712, the early A4 event detection is confirmed at block 714. If the A2 event time interval has shortened, an indicator of an increasing or imminently increasing heart rate, a relatively early A4 event can be expected. Control circuit 206 starts an AV pacing interval at block 716 to synchronize the next ventricular pacing pulse with the detected atrial systolic A4 event. When the AV pacing interval is started, the LR pacing interval may be stopped to allow the timing of the ventricular pacing pulse to be controlled by the AV pacing interval. The AV pacing interval started at block 716 may be adjusted based on the A2 interval shortening determined at block 712, e.g., according to the methods described in conjunction with FIG. 8.

If the A2 event time interval is not determined to be shortened at block 712, the early A4 event detection is not confirmed at block 718. The early A4 event detection may be a signal caused by patient physical activity or other motion sensor signal noise. The AV pacing interval is not started if the early A4 event is not confirmed. The LR pacing interval is allowed to continue running. Control circuit 206 may continue to monitor for a later A4 event signal at block 720.

A late A4 event may be detected at block 720 based on criteria applied by control circuit 206 for detecting a late A4 event. For example, if the motion sensor signal crosses an A4 event detection threshold amplitude after the A4 refractory period expires, the A4 event is detected as a late A4 event. In other examples, a threshold amplitude crossing after a predetermined time interval after the expiration of the A4 refractory period, e.g., after an A3 event window expires, a late A4 event detection is made. If a late A4 event detection is detected at block 720, the A4 event is confirmed at block 714 based on the relatively "late" timing of the A4 event according to the criteria applied at block 720. An AV pacing interval is started at block 716. The A2 event timing may not be checked for confirming the late A4 event. The A4 refractory period and A4 detection threshold amplitude may be considered to be properly set for detecting a true A4 event. If an A4 event is detected and the subsequent AV pacing interval expires, a ventricular pacing pulse is delivered at block 724.

If an early A4 event is detected but not confirmed and/or no late A4 event is detected, the LR interval expires without an A4 event being detected ("yes" branch of block 722). A ventricular pacing pulse is delivered at block 724 at the LR pacing interval. While not shown explicitly in FIG. 10, it is recognized that if an intrinsic R-wave is sensed by sensing circuit 204 during the LR pacing interval or during the AV pacing interval, the scheduled pacing pulse is withheld, and the process returns to block 702. The sensed R-wave is identified as the next ventricular electrical event.

Figure 11A:
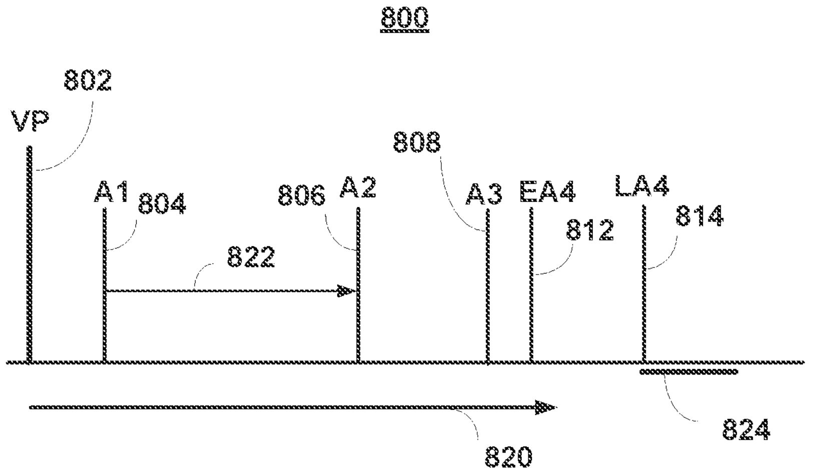
FIG. 11A is a timing diagram depicting one method performed by an intracardiac ventricular pacemaker for distinguishing early and late atrial systolic events detected from a motion sensor signal.

FIG. 11A is a timing diagram 800 depicting one method performed by pacemaker 14 for distinguishing early and late A4 events. In the method of FIG. 10, the A4 refractory period set at block 706 may be set based on an expected time of the A3 event, e.g., as described in conjunction with FIG. 5, and may be adjusted in response to changes in the A2 event time interval as described in conjunction with FIG. 8. The A4 refractory period may expire before, at or later than an expected time of the A3 event in various instances. The distinction between an "early" A4 event detection and a "late" A4 event detection may be based on the expiration time of the A4 refractory period when it is set to expire later than the expected A3 event time.

In FIG. 11A, a ventricular pacing pulse 802 is identified as a ventricular electrical event and starts an A4 refractory period 820 set to expire after an expected time of the A3 event 808. An A2 event 806 is detected during the A4 refractory period 820. In some cases, the A1 event 804 is also detected during the A4 refractory period and used to determine the A2 event time interval 822. In other examples, the A2 event time interval may be measured from the ventricular electrical event VP 802 to the A2 event 806.

The A3 event 808 may be detected during the A4 refractory period based on a motion sensor signal threshold amplitude crossing so that the next event detected from the motion sensor signal can be identified as an A4 event with increased confidence when one, two or all three of the preceding ventricular A1, A2 and A3 events have been detected during the A4 refractory period 820. Detection of the A3 event, however, may not be required before detecting the A4 event.

In the example shown, an A4 event 812 is detected before the expiration of the A4 refractory period 820 and is therefore identified as an early A4 event (EA4). The A4 event 812 may be detected based on a motion sensor signal crossing of the A4 event detection threshold amplitude, which may be a decaying or multi-level threshold having a higher amplitude during the A4 refractory period 820 than after the A4 refractory period 820. In order to confirm the early A4 event 812 detected during the A4 refractory period 820, the A2 event time interval 822 is compared to A2 interval shortening criteria. For example, A2 event time interval 822 may be compared to one or more preceding A2 event time intervals, a running average A2 event time interval, or other threshold for detecting A2 event time interval shortening.

If A2 event time interval shortening is detected, justifying the early occurrence of the A4 event, the early A4 event 812 is confirmed as the A4 event, and an AV pacing interval is started. If the A2 event time interval 822 is not determined to be shortening, the early A4 event 812 is not confirmed. The LR pacing interval started upon VP 802 continues to run as described in conjunction with FIG. 10; no AV pacing interval is started.

An A4 event detected after expiration of the A4 refractory period 820 is detected as a late A4 event (LA4) 814. When the late A4 event 814 is detected outside the A4 refractory period, no confirmation of the A4 event is required based on the A2 event time interval. The LR pacing interval may be cancelled, and a pacing escape timer or counter included in pace timing circuit 242 may be set to the AV pacing interval 824 in response to the late A4 event 814.

Figure 11B:
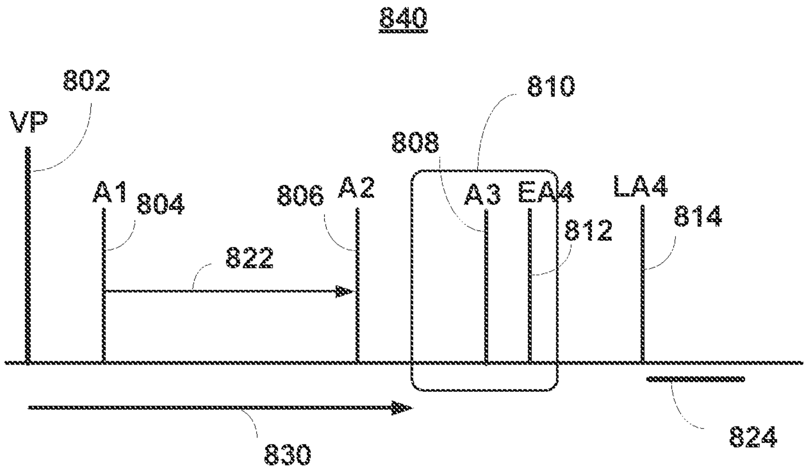
FIG. 11B is a timing diagram illustrating an alternative method for distinguishing between early and late atrial systolic events detected from a motion sensor signal for controlling ventricular pacing.

FIG. 11B is a timing diagram 840 illustrating an alternative method for discriminating between early and late A4 events for use in confirming A4 event detections and controlling ventricular pacing. In some examples, the time interval to an A3 event may be determined, e.g., from the averaged motion sensor signal as shown in FIG. 7. The A4 refractory period 830 may be set to expire prior to an expected time of the A3 event 808 (but later than the expected time of the A2 event 806). In some examples, the A4 refractory period 830 may initially be set to expire after the expected time of the A3 event but may be adjusted shorter than an expected A3 event time in response to a decreasing trend of the A2 event time interval, e.g., as described in conjunction with FIGS. 8 and 10.

When the A4 refractory period 830 expires earlier than an expected A3 event time, an A3 event window 810 may be used to distinguish an early A4 event 812 from a late A4 event 814. For example, if an A4 event detection 812 occurs after expiration of an A4 refractory period 830, but before expiration of an A3 window 810, the A4 event 812 is confirmed as an early A4 event based on an analysis of the A2 event time interval 822 before starting an AV pacing interval in response to the early A4 event 812. If the A2 event time interval 822 is determined to be shortened compared to one or more preceding A2 event time interval(s) or other A2 event time shortening criteria, the early A4 event 812 is confirmed as an A4 event. Otherwise the early A4 event 812 is ignored for the purposes of setting an AV pacing interval. The LR pacing interval (not explicitly shown in FIG. 11B) that is started upon VP 802 is allowed to continue running.

If a late A4 event 814 is detected after the expiration of the A3 window 810, confirmation of the late A4 event 814 based on the A2 event time interval 822 may not be required. An AV pacing interval 824 may be set immediately in response to the late A4 event detection.

Figure 12:
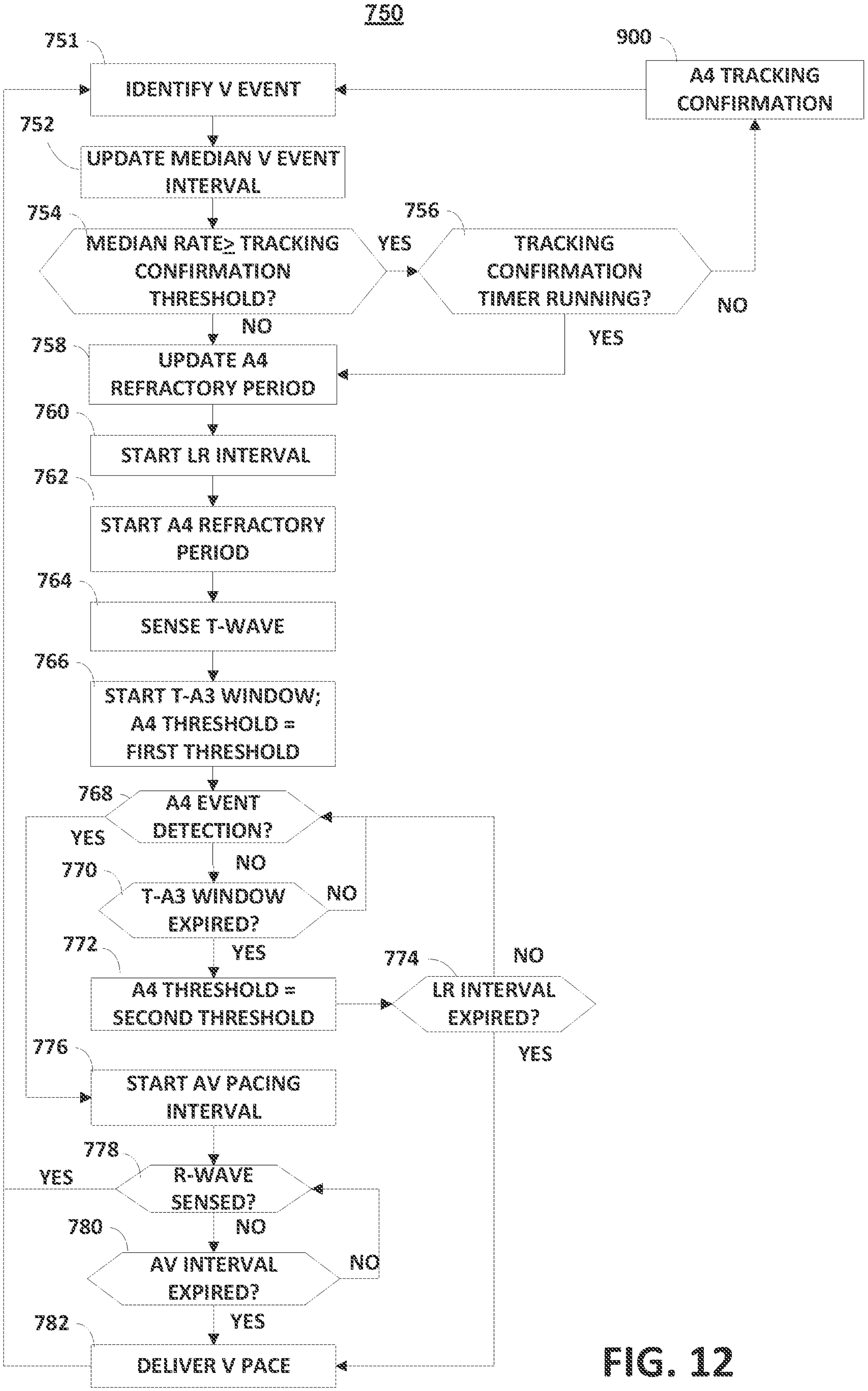
FIG. 12 is a flow chart of a method performed by an intracardiac ventricular pacemaker for detecting an atrial systolic event from a motion sensor signal and controlling ventricular pacing according to another example.

FIG. 12 is a flow chart 750 of a method performed by an intracardiac ventricular pacemaker for detecting an atrial systolic event from a motion sensor signal and controlling ventricular pacing according to another example. At block 751, a ventricular electrical event, paced or sensed, is identified by control circuit 206. Control circuit 206 determines a ventricular event interval ending on the identified ventricular event and updates a running median ventricular event interval at block 752. The ventricular event interval may be determined as the time interval from the most recent preceding ventricular event, either a sensed R-wave or a ventricular pacing pulse, to the current ventricular event, sensed or paced. The ventricular event interval may be stored in a circulating buffer in memory 210 that stores a predetermined number of the most recent ventricular event intervals, for example six to eight ventricular event intervals.

Control circuit 206 determines the running median ventricular event interval from the buffered ventricular event intervals. In one example, the median ventricular event interval is determined from six to eight buffered event intervals but fewer or more event intervals may be used to determine the median ventricular event interval. In some examples, a trimmed median may be determined by eliminating a shortest and/or longest ventricular event interval before determining the median interval. In other examples, a different measure of center of the ventricular event intervals other than the median may be determined at block 752, such as a mode or average.

At block 754, the control circuit 206 compares the ventricular rate corresponding to the median ventricular event interval to a tracking confirmation threshold rate. If the median rate is equal to or greater than the tracking confirmation threshold rate, the control circuit 206 may execute an A4 tracking confirmation process at block 900. The threshold rate may be 100 beats per minute in one example. In other examples, the control circuit 206 may compare the median ventricular event interval directly to a tracking confirmation threshold interval. For instance, if the median ventricular event interval is equal to or less than 600 ms, corresponding to a ventricular rate of 100 beats per minute or more, the A4 tracking confirmation process is performed at block 900. The A4 tracking confirmation process is described below in conjunction with FIG. 13.

In some examples, the A4 tracking confirmation process is performed in response to the ventricular rate being equal to or greater than the tracking confirmation threshold only if A4 tracking has not been confirmed for at least a predetermined time interval. As such, control circuit 206 may determine if a tracking confirmation timer is running at block 756. As described in conjunction with FIG. 13, the tracking confirmation timer may be started after tracking of A4 events is confirmed. If the median ventricular rate remains above a tracking confirmation threshold rate, e.g., equal to or greater than 100 beats per minute, the A4 tracking confirmation process at block 900 may be repeated but only after the tracking confirmation timer has expired. In one example, the tracking confirmation timer is set to 90 seconds, but it may be set to greater than or less than 90 seconds in other examples.

In some examples, the tracking confirmation timer is an adjustable timer. Control circuit 206 may be configured to increase the time interval that the tracking confirmation timer is set to after A4 tracking has been repeatedly confirmed. For example, if A4 tracking has been confirmed a second time, ninety seconds after the first A4 tracking confirmation, the timer may be set to 180 seconds or another interval longer than ninety seconds, and so on. As long as the median ventricular rate remains at or above the tracking confirmation threshold rate, the A4 tracking confirmation at block 900 may be repeated each time the tracking confirmation timer expires, as determined at block 756. If the tracking confirmation timer is still running at block 756, the process of FIG. 12 advances to block 758 ("yes" branch of block 756).

If a tracking confirmation timer is not running, "no" branch of block 756, A4 tracking confirmation is performed at block 900. After performing the A4 tracking confirmation process as described below in conjunction with FIG. 13, control circuit 206 may return to the process of flow chart 750 at block 751.

As long as the median ventricular rate is not equal to or greater than the tracking confirmation threshold rate at block 754 (or the tracking confirmation timer is still running), control circuit 206 controls pacemaker 14 to operate in an atrial-tracking ventricular pacing mode (also referred to herein as an atrial-synchronized ventricular pacing mode). Control circuit 206 uses the median ventricular event interval updated at block 752 to update the A4 refractory period at block 758. In the example of FIG. 12, the A4 refractory period is set based on the median ventricular event interval. For instance, the A4 refractory period may be set to the median ventricular event interval less a predetermined, fixed time interval, e.g., the median ventricular event interval minus 100 ms. In some examples, the A4 refractory period is set based on the median ventricular event interval up to a maximum upper limit. For instance, the maximum upper limit of the A4 refractory period may be set to 600 ms, 650 ms or 700 ms in various examples. Other techniques described above for establishing the A4 refractory period or techniques generally disclosed in the above-incorporated U.S. patent application Ser. No. 15/280,339, filed Sep. 29, 2016 and granted as U.S. Pat. No. 10,449,336 (Splett, et al.), may be used for updating the A4 refractory period at block 758.

At block 760, control circuit 206 starts the ventricular LR pacing interval in response to the ventricular event (paced or sensed) identified at block 751. The LR interval is started as a pacing escape interval that controls the timing of a ventricular pacing pulse in the absence of a detected event from the motion sensor signal. The A4 refractory period is started at block 762. The A4 refractory period may be the updated refractory period determined at block 758 based on the currently determined median ventricular event interval. In other examples, however, the A4 refractory period started at block 762 may be the A4 refractory period that was updated on the preceding ventricular cycle. The A4 refractory period updated at block 758 may be applied after the next ventricular event on the next cardiac cycle, e.g., due to processing timing. During the A4 refractory period, an A4 event is not detected or is at least ignored for the purposes of setting an AV interval.

Sensing circuit 204 may include a T-wave detector configured to sense T-waves from a cardiac electrical signal received from the patient's heart 8, e.g., via electrodes 162 and 164 shown in FIG. 2A, coupled to sensing circuit 204. Alternatively, control circuit 206 may be configured to detect T-waves from a digitized cardiac electrical signal received from sensing circuit 204. At block 764, a T-wave (attendant to ventricular repolarization) is sensed from the cardiac electrical signal. An A3 window is started at block 766. The A3 window may be a time interval from the sensed T-wave to an expected time of the A3 event or after the expected A3 event but before the expected A4 event time. The duration of the A3 window may be established based on a previously determined average A3 event time relative to the T-wave, e.g., as described in conjunction with FIG. 7.

In other examples, the duration of the A3 window may be set manually. A filtered motion sensor signal and a filtered cardiac electrical signal output from sensing circuit 204 may be transmitted from pacemaker telemetry circuit 208 to external device 20 for display to a clinician. A clinician may observe the A3 event timing in the motion sensor signal relative to the T-wave timing in cardiac electrical signal and determine an appropriate duration of the A3 window. The user may program the A3 window using external device 20. The A3 window may be stored in memory 210 for use by control circuit 206.

After expiration of the A4 refractory period, the control circuit 206 waits for an A4 event detection at block 768. The A4 event detection may be made during or after the A3 window in some examples. The A4 event detection is based on the motion sensor signal crossing an A4 detection threshold amplitude. In some examples, a higher A4 detection threshold is applied during the A3 window than after the A3 window expires. The A3 window may or may not begin before expiration of the A4 refractory period, but is likely to extend beyond the expiration of the A4 refractory period. If the A4 refractory period expires before or during the A3 window, the control circuit 206 may set the A4 detection threshold amplitude to a first value during the A3 window then adjust the A4 detection threshold amplitude to a second value lower than the first value in response to the A3 window expiring. A higher A4 detection threshold amplitude is applied during the A3 window to enable detection of fused A3 and A4 event signals while still avoiding oversensing of the A3 event as an A4 event. An automatically adjusted A4 detection threshold amplitude may be used in detecting the A4 event at block 766 as generally disclosed in the above-incorporated U.S. patent application Ser. No. 15/280,339, filed Sep. 29, 2016 and granted as U.S. Pat. No. 10,449,366 (Splett, et al.).

If an A4 event detection occurs, "yes" branch of block 768, the pace timing circuit 242 starts the AV pacing interval at 776. If an A4 event detection does not occur before the A3 window expires, as determined at block 770, control circuit 206 may adjust the A4 detection threshold amplitude to a second lower threshold at block 772. If the LR interval has not expired (block 774), and an A4 event is detected (block 768) in response to the motion sensor signal crossing the second lower threshold after the A3 window expires, the AV pacing interval is started at block 776. If the AV interval expires before an R-wave is sensed (blocks 778 and 780), the ventricular pacing pulse is delivered at block 782, synchronized to the detected A4 event at the AV interval. If the LR interval expires before an A4 event detection is made, as determined at block 774, the ventricular pacing pulse is delivered at block 782, and the process returns to block 751.

The control circuit 206 controls the pulse generator to deliver ventricular pacing pulses tracked to events detected from the motion sensor signal based on the A4 detection threshold amplitude. In some instances, however, other motion sensor signal events may cross the A4 detection threshold amplitude and be falsely detected as an A4 event and tracked by a ventricular pacing pulse. A false or oversensed event may be an A3 event corresponding to ventricular passive filling, motion due to patient physical activity, or environmental vibrations causing noise signals in the motion sensor signal, as examples. As such, events detected as A4 events and tracked by ventricular pacing pulses at block 768 may not be true A4 events. Ventricular tracking of non-atrial events detected from the motion sensor signal may lead to an increased ventricular pacing rate. As indicated above, if the median ventricular event interval corresponds to a ventricular rate greater than the A4 tracking confirmation rate, control circuit 206 performs an A4 tracking confirmation process at block 900. After performing the A4 tracking confirmation process, the control circuit 206 may re-enter the process of flow chart 750 at block 751.

Figure 13:
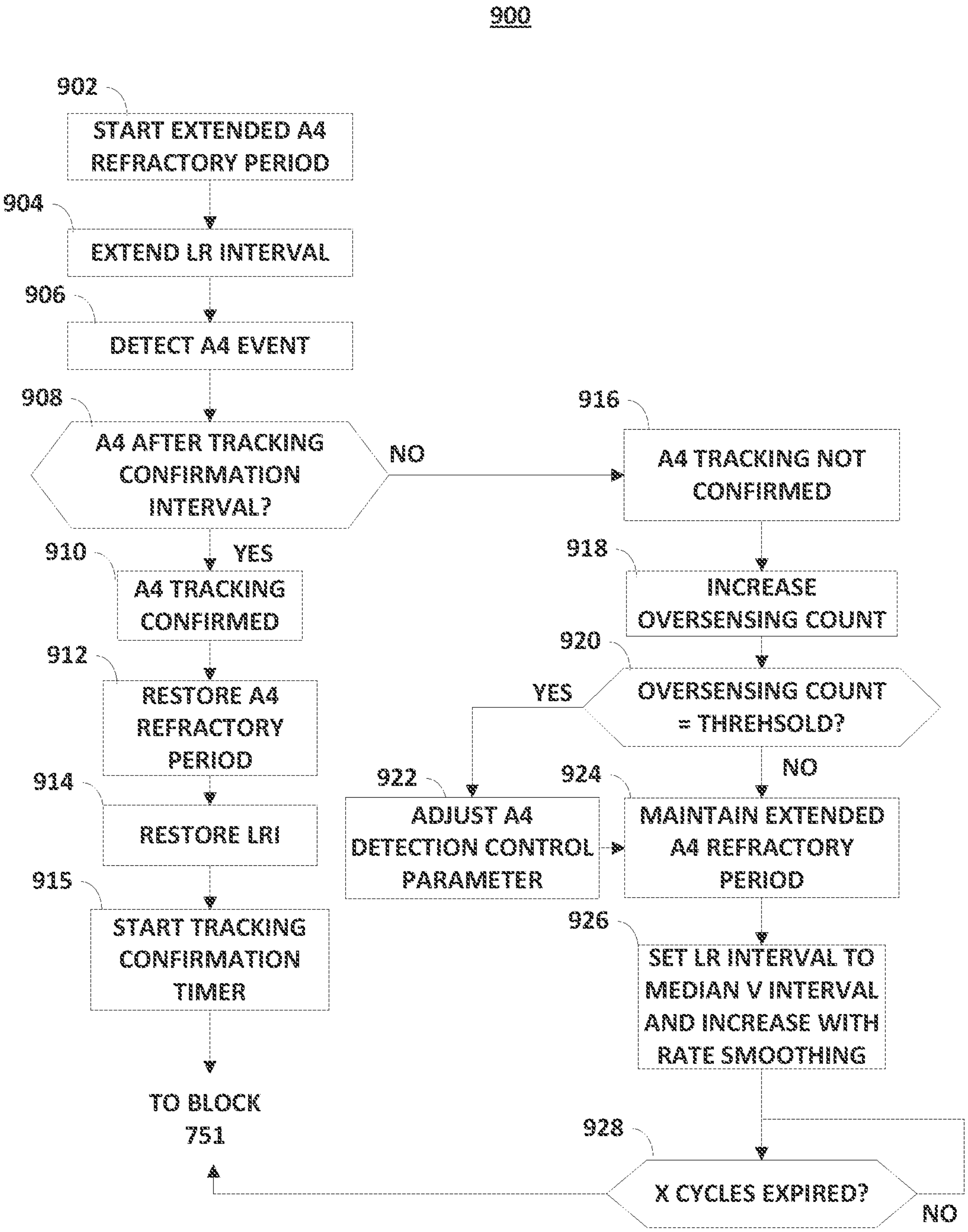
FIG. 13 is a flow chart of a method for performing atrial tracking confirmation by the intracardiac pacemaker according to one example.

FIG. 13 is a flow chart 900 of a method for performing A4 tracking confirmation by intracardiac pacemaker 14 according to one example. The process of flow chart 900 may be performed at like-numbered block 900 of FIG. 12 in response to the median ventricular rate being greater than or equal to an A4 tracking confirmation threshold rate. In some instances, the atrial event detector circuit 240 of control circuit 206 (FIG. 3), may oversense A3 events as A4 events. In this situation, the AV interval is started in response to the oversensed A3 event, which corresponds to cardiac motion during passive ventricular filling. Pacing the ventricle at an AV interval started in response to the A3 ventricular event (instead of the A4 atrial event) may lead to accelerated ventricular pacing and a loss of atrioventricular synchrony.

To avoid this situation, as the median ventricular event interval decreases, e.g., to less than a tracking confirmation threshold interval, A4 event tracking confirmation may be performed. The A4 event tracking confirmation may determine that inappropriate tracking of an oversensed motion sensor signal that does not correspond to the atrial A4 event, such as an oversensed A3 event, another ventricular motion sensor signal event, or other noise present in the motion sensor signal, is occurring, leading to the increased ventricular pacing rate.

At block 902, control circuit 206 starts an extended A4 refractory period set in response to the most recently identified ventricular electrical event (at block 751 of FIG. 12). The extended A4 refractory period may be set based on a determined time interval from a ventricular event to the detected A4 event (V-A4 interval). In some examples, control circuit 206 may determine the current V-A4 interval, and set the A4 refractory period to a fixed interval, e.g., 100 ms, longer than the V-A4 interval. In other examples, an average or median value of the most recent V-A4 intervals, e.g., three most recent V-A4 intervals, may be determined. The extended A4 refractory period may be set to be a predetermined fixed interval longer than the average or median V-A4 interval.

The extended A4 refractory period is set at block 902 to an interval that is longer than the expected time to the next A4 event. The extended A4 refractory period is set longer than the time interval from the ventricular event to the next expected A4 event to intentionally cause the next expected A4 event detection to occur during the A4 refractory period. By setting an extended A4 refractory period, the control circuit 206 causes the next expected A4 event detection to be a refractory event such that no AV interval is started, and a ventricular pacing pulse that would otherwise be scheduled at the AV interval following the next expected A4 event detection is withheld.

At block 904, control circuit 206 starts an extended LR interval in response to the most recently identified ventricular electrical event. The extended LR interval may be set based on the median ventricular event interval in some examples. For instance, the extended LR interval may be set to at least twice the median ventricular event interval. In one example, the extended LR interval is set to twice the median ventricular event interval plus a predetermined fixed interval, e.g., 100 ms. By setting the LR interval to an extended interval, control circuit 206 prevents a ventricular pacing pulse from being delivered during the next atrial cycle. As described below in conjunction with the timing diagram of FIG. 14, this effective withholding of a ventricular pacing pulse by extending the A4 refractory period and the LR interval for one cardiac cycle eliminates any ventricular A1, A2 and A3 events from the motion sensor signal for one cycle to allow identification of the atrial A4 event. If A3 events are being oversensed as A4 events, leading to the increased median ventricular rate, the ventricular A3 event is effectively inhibited during the A4 tracking confirmation process by withholding a ventricular pacing pulse for one cardiac cycle. The A1, A2 and A3 events will be absent from the motion sensor signal (assuming an intrinsic ventricular beat does not occur) during the one cardiac cycle.

In a patient with AV block, if pacemaker 14 is correctly tracking A4 events at the time that the A4 tracking confirmation process is started, the rate of the A4 events is expected to be relatively steady such that the next A4 event is expected to occur during the extended A4 refractory period and the A4 event after that is expected near the end of the extended LR interval when the extended LR interval is set based on the median ventricular event interval, e.g., twice the median ventricular event interval plus 100 ms (or other offset). If A3 events (or motion sensor signal noise such as patient physical activity or environmental vibrations) have been oversensed leading to inappropriate tracking of the A3 event (or motion sensor signal noise) instead of the A4 event, the next true A4 event may occur relatively early after the extended A4 refractory period. The A3 event (or noise signal) previously being tracked is now masked by the extended A4 refractory period. The true A4 event, which may have coincided with a ventricular pacing pulse or occurred during the A4 refractory period set following the ventricular pacing pulse, may be unmasked during the A4 tracking confirmation process. An event detected from the motion sensor signal after the extended A4 refractory period at block 906 is an atrial A4 event with relatively high certainty since the ventricular pacing pulse is effectively withheld for one cardiac cycle, thereby removing ventricular A1, A2 and A3 event signals from the motion sensor signal. If events detected from the motion sensor signal are true atrial A4 events, the detected event rate should not change when a ventricular pacing pulse is withheld or delayed. Therefore the timing of the A4 event detected after the extended A4 refractory period and during the extended LR interval is used to confirm or not confirm proper A4 tracking of ventricular pacing delivered prior to the A4 tracking confirmation process.

For example, upon detecting an A4 event at block 906 after the extended A4 refractory period, control circuit 206 determines if the detected A4 event occurs relatively early after the extended A4 refractory period or as expected near the end of the extended LR interval. If events being detected from the motion sensor signal and tracked by ventricular pacing pulses are true atrial A4 events, the detected A4 event should occur at a rate that corresponds to the most recently determined median ventricular event interval. The A4 event detected after the extended A4 refractory period is expected to occur at two atrial cycle lengths since the most recent preceding detected A4 event (with one refractory A4 event in between during the extended A4 refractory period). Two atrial cycle lengths are equal to twice the median ventricular event interval if proper atrial A4 tracking was occurring prior to starting the tracking confirmation process. The median ventricular event interval represents the recent ventricular pacing rate that was tracking the events detected from the motion sensor signal. If the detected events being tracked by ventricular pacing pulses are not true atrial A4 events, the A4 event detected after the extended A4 refractory period will occur at a rate that does not correspond to the median ventricular event interval rate.

In one example, control circuit 206 determines if the detected A4 event at block 906 occurs later than a tracking confirmation interval after the most recently identified ventricular event (or after the most recent motion sensor signal event detected before the extended A4 refractory period). The tracking confirmation interval may be based on the median ventricular event interval, e.g., twice the median ventricular event interval less a predetermined time interval. If the A4 event detected after the extended A4 refractory period occurs at twice the median ventricular event interval since the most recent preceding A4 event detected before the extended A4 refractory period, both detected events are true A4 events occurring at the expected atrial event rate.

In other examples, control circuit 206 may determine if the A4 event detected after extending the A4 refractory period occurs within a predetermined time of the expected A4 event time, e.g., within 100 ms before or after the expected A4 event time. For instance, control circuit 206 may determine if the detected A4 event occurs within a predetermined time interval of the expiration of the extended LR interval, which is set based on the median ventricular event interval. The extended LR interval may be set to twice the median ventricular event rate plus 100 ms (or other fixed time interval). In this illustrative example, control circuit 206 may determine that, if the A4 event detected at block 906 is within 200 ms before the expiration of the extended LR interval, e.g., 100 ms before or after the expected A4 time, A4 tracking is confirmed at block 910. The event detected before the extended A4 refractory period is a true A4 event based on the timing of the A4 event detected after the extended refractory period.

If the A4 event is detected earlier than 200 ms (or other predetermined time interval) before the expiration of the extended LR interval, A4 tracking is not confirmed at block 916. The earlier than expected occurrence of the unmasked A4 event is evidence of possible A3 or other motion sensor signal noise oversensing. The most recent event detected from the motion sensor signal prior to the extended A4 refractory period is not a true A4 event. The accelerated ventricular pacing may have been tracking a ventricular event of the motion sensor signal or other noise rather than the atrial A4 event.

If A4 tracking is confirmed at block 910, the AV interval may be started in response to the detected A4 event detected after the extended A4 refractory period for controlling the next ventricular pacing pulse timing according to the atrial-synchronized ventricular pacing mode. Control circuit 206 restores the A4 refractory period to its previous value, e.g., based on the median ventricular event interval, at block 912.

The LR interval is restored at block 914 to its previous value that was in effect prior to extending the LR interval for the tracking confirmation process. The previous LR interval may be a fixed LR interval such as 1000 ms, corresponding to a lower, base pacing rate of 60 beats per minute. In some examples, the LR interval may be restored to its previous value with rate smoothing enabled. For example, the LR interval may be restored by setting the LR interval to the median ventricular event interval and gradually increasing the LR interval once every two to four beats by a predetermined increment, e.g., 50 ms, to the previous LR interval. Pacemaker 14 resumes tracking A4 events and delivering atrial-synchronized ventricular pacing.

In some examples, control circuit 206 may start a tracking confirmation timer or counter at block 915 to limit how often the A4 tracking confirmation process is repeated. Referring again to FIG. 12, if the ventricular rate (based on the updated median ventricular event interval) is greater than the tracking confirmation threshold rate at block 754 for a series of consecutive ventricular events, the A4 tracking confirmation process could be re-triggered repeatedly on a beat-by beat basis. To avoid unnecessary repetition of the A4 tracking confirmation process during periods of a sustained ventricular rate above the A4 tracking confirmation rate, the tracking confirmation timer may be set at block 915 to limit how soon tracking confirmation is repeated again after A4 tracking has been confirmed at block 910.

For example, the tracking confirmation timer may be set to count down 30 seconds, one minute, 90 seconds, two minutes or other pre-determined time interval. The A4 tracking confirmation process is not performed in response to the median ventricular rate being greater than the tracking confirmation threshold rate unless the tracking confirmation timer is no longer running. For example, tracking confirmation may not be performed more frequently than every ninety seconds. In other examples, the A4 tracking confirmation process may be repeated sooner, before the tracking confirmation timer expires, if the ventricular rate increases from the rate that previously triggered the A4 tracking confirmation. For example, if the ventricular rate increases from 100 beats per minute to 120 beats per minute, A4 tracking confirmation may be performed earlier than 90 seconds after a preceding tracking confirmation. In other instances, the tracking confirmation timer may be set to an increased time interval if tracking has been confirmed during multiple consecutive tracking confirmation processes.

Referring again to FIG. 13, if A4 tracking is not confirmed at block 916, due to an early A4 event detection during the extended LR interval, control circuit 206 may increase an oversensing counter at block 918. The oversensing counter may be used to track the number of times A4 tracking is not confirmed. The oversensing counter may be initialized to zero and increased by one each time A4 tracking is not confirmed.

The oversensing counter value may be compared to a threshold value at block 920. If the number of times that A4 tracking has not been confirmed is less than an oversensing count threshold value, "no" branch of block 920, control circuit 206 maintains the extended A4 refractory period to temporarily limit the maximum atrial tracking rate of ventricular pacing pulses and promote proper A4 tracking. In one example, control circuit 206 is configured to apply the extended A4 refractory period following each ventricular event that occurs during a predetermined time interval or for a predetermined number of ventricular events. For example, the extended A4 refractory period may be applied following the next 64 ventricular events, thereby limiting the maximum tracking rate for at least 64 cardiac cycles. In other examples, more than or less than 64 ventricular events may be followed by the extended A4 refractory period.

During this temporary extension of the A4 refractory period, only A4 events occurring after the extended A4 refractory period may be tracked for setting the AV interval and delivering atrial synchronized ventricular pacing. A4 events occurring earlier than the A4 refractory period expiration are not tracked. For instance, if the extended A4 refractory period is set to 667 ms or longer, the maximum atrial-tracking rate is 90 beats per minute or less.

If the atrial rate is faster than the maximum tracking rate, the ventricular pacing rate may be controlled by the ventricular LR interval. In order to avoid a sudden rate change from the median ventricular event interval that triggered the A4 confirmation process, control circuit 207 may adjust the LR interval to the median ventricular event interval at block 926. In some examples, the LR interval is set to the median ventricular event interval and then gradually increased using rate smoothing. The LR interval may be gradually increased to its previous setting that was in effect prior to the A4 tracking confirmation process. For example, the LR interval may be set to 1000 ms or longer to control a minimum ventricular rate. Control circuit 206 may adjust the LR interval to the median ventricular event interval at block 926 then increase the LR interval by a short increment, e.g., 25 to 50 ms, once every few beats, e.g., once every 2 to 5 beats. To illustrate, if the median ventricular event interval is 600 ms at the time that the A4 tracking confirmation process was triggered, the LR interval is set to 600 ms at block 924 and held at 600 ms for three ventricular cycles. The LR interval is increased to 650 ms for the next three ventricular cycles, 700 ms for the next three ventricular cycles after that, and so on until the LR interval is restored to its previous setting.

This rate smoothing allows the ventricular rate, which may have been artificially high due to tracking the ventricular A3 event rather than the atrial A4 event, to gradually be decreased while the A4 refractory period is temporarily extended. The slowing of the ventricular paced rate and the extended A4 refractory period promote A4 event tracking to be regained at a lower heart rate. After the extended A4 refractory period has been applied for a predetermined number of ventricular cycles, e.g., 64 cycles, as determined at block 928, the A4 tracking confirmation process of FIG. 13 may be exited. Control circuit 206 may return to block 751 of FIG. 12 to resume atrial-synchronized ventricular pacing, using an updated A4 refractory period set based on the updated median ventricular event interval as described above. The oversensing of motion sensor signal events that are not true atrial A4 events, e.g., A3 event oversensing, has been interrupted by the A4 tracking confirmation process, promoting proper A4 tracking to be regained. If the median ventricular rate increases above the A4 tracking confirmation rate threshold again, tracking confirmation at block 900 will be repeated.

If A4 tracking is repeatedly not confirmed such that the oversensing counter value reaches a threshold count at block 920 ("yes" branch), control circuit 206 may adjust an A4 detection control parameter to be used upon returning to the method of flow chart 750. In one example, a minimum A4 refractory period is set to limit the maximum atrial tracking rate. For example, the minimum A4 refractory period may be set to 600 ms to limit the maximum atrial-tracked ventricular pacing rate to 100 beats per minute. In other examples, the minimum A4 refractory period may be set to 667 ms to limit the atrial-tracked ventricular pacing rate to 90 beats per minute. In this way, A4 event tracking is performed at relatively low heart rates when A4 event detection may be more reliable than during high heart rates.

In other examples, instead of or in addition to setting a minimum A4 refractory period that limits the maximum atrial tracking rate at block 922, one or more other A4 event detection parameters may be adjusted at block 922 to promote reliable A4 event detection and tracking. For example, the A4 detection threshold amplitude may be adjusted at block 922. If A3 events are being oversensed, increasing the A4 detection threshold amplitude, as least during the A3 window, may reduce the likelihood of A3 oversensing and promote proper A4 event tracking. In some cases, reducing the A4 detection threshold amplitude at block 922 may improve A4 event detection and A4 tracking. For instance, reducing the second A4 detection threshold that is used after the A3 window may enable more reliable A4 event detection.

In another example, the A3 window may be adjusted at block 922. The A3 window may be lengthened to ensure the A3 event signal occurs during the A3 window, when the A4 detection threshold amplitude is set to the first, higher amplitude. If the A3 window is too short, the A3 event may occur after the A3 window expires and the A4 detection threshold amplitude is decreased to the second, lower amplitude, potentially leading to A3 event oversensing. The start time and/or end time of the A3 window may be adjusted.

In yet another example, the A3 detection threshold amplitude may be adjusted. The A3 window may be set automatically by control circuit 206 based on detecting the A3 event, determining the actual A3 time interval, and setting the A3 window based on the determined A3 time interval. An adjustment of the A3 detection threshold amplitude may change the timing of the detected A3 event following the T-wave, resulting in a change in the automatically set A3 window, which may reduce the likelihood of A3 event oversensing.

Adjustment of any control parameter that reduces the likelihood of oversensing A3 events or other motion sensor signal noise as A4 events may be performed at block 922 to promote reliable A4 event detection and A4 event tracking. One or more parameters may be adjusted. After adjusting the A4 detection control parameter(s) at block 922, control circuit 206 may set the LR interval at block 926 to the median ventricular event interval and gradually increase the LR interval using rate smoothing as described above. The control circuit 206 may or may not wait the predetermined number of cardiac cycles at block 928. In some cases, control circuit 206 returns directly to block 751 after adjusting the LR interval at block 926 to use the control parameters adjusted at block 922 in the atrial-synchronized ventricular pacing mode of FIG. 12. In the example shown in FIG. 13, after adjusting the A4 detection control parameters at block 922, the control circuit 206 may still apply the extended A4 refractory period temporarily for x cycles, e.g., 64 cycles, at block 928 to interrupt the non-A4 event oversensing and promote restoration of proper A4 event detection before returning to block 751 of FIG. 12. The A4 tracking confirmation process of FIG. 13 may be used in conjunction with any of the atrial-synchronized ventricular pacing techniques described above or as generally disclosed in U.S. patent application Ser. No. 15/342,699, filed Nov. 3, 2016 and granted as U.S. Pat. No. 10,286,214 (Demmer, et al.), incorporated herein by reference in its entirety.

Figure 14:
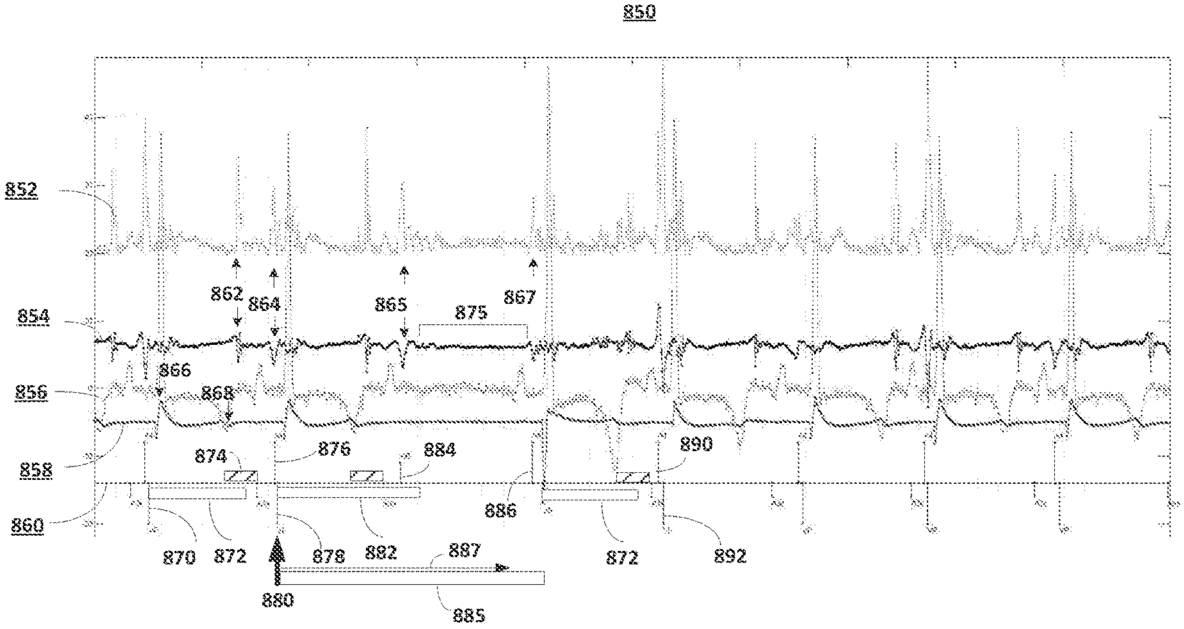
FIG. 14 is a timing diagram illustrating confirmation of atrial event tracking according to one example.

FIG. 14 is a timing diagram 850 illustrating confirmation of A4 event tracking according to one example. A raw motion sensor signal 854 and a filtered, amplified and rectified motion sensor signal 852 obtained from the raw motion sensor signal 854 are shown. The raw and filtered motion sensor signals 854 and 852 include A2 event signals 862 followed by fused A3-A4 event signals 864 during each cardiac cycle. A raw surface electrocardiogram (ECG) signal 856 and a raw cardiac electrogram (EGM) signal 858 produced from electrical signals received via the housing-based electrodes of pacemaker 14 are shown including R-waves 866 followed by T-waves 868.

In response to a ventricular event (Vpace 870), an A4 refractory period 872 is started. The T-wave 868 is detected, and a A3 window 874 is started. In other examples the A3 window 874 may be set to start at the ending time of the A4 refractory period 872, which may be set to a nominal value selected to encompass the A1 and A2 events with a high degree of certainty. The A3 window is set to have an ending time prior to an expected A4 event. For example, the A4 refractory period 872 may be 600 to 800 ms in duration after an identified ventricular electrical event, and the A3 window 874 may be 200 to 300 ms in duration, as examples. The A4 event 864 (fused with A3 in this example) is detected, as indicated by A4 event marker 876. A higher A4 detection threshold amplitude may be applied during the A3 window 874, and a lower A4 detection threshold amplitude may be applied after the A3 window 874. Upon the A4 event detection 876, an AV interval (not shown in FIG. 14) is started, e.g., an 8 to 20 ms AV interval. The ventricular pacing pulse 878 is delivered upon expiration of the AV interval.

A median ventricular event interval is updated in response to each ventricular event as described in conjunction with FIG. 12. Upon delivering ventricular pacing pulse 878, control circuit 206 determines that the median ventricular event interval corresponds to a ventricular rate that is equal to or greater than the A4 tracking confirmation rate threshold. Control circuit 206 starts the A4 tracking confirmation process at arrow 880 by setting the A4 refractory period 882 to an extended interval. For example, the extended A4 refractory period 882 may be set to 100 ms longer than the interval between the previous Vpace 870 and detected A4 event 876. In addition to extending the A4 refractory period 882, control circuit 206 may set the ventricular LR interval 885 to an extended interval. In one example, extended LR interval 885 is set to twice the median ventricular event interval plus 100 ms.

The next A4 event 865 occurs during the extended A4 refractory period 882, as indicated by refractory A4 marker 884. Control circuit 206 does not start an AV interval in response to the refractory A4 event. Since the ventricular pacing pulse is withheld following the refractory A4 event 865, a baseline interval 875 occurs on the motion sensor signal 854 (A1, A2, and A3 ventricular events are absent due to withholding of the ventricular pacing pulse for one cycle). The next A4 event 867 is a true A4 event that is not fused with the absent A3 event. The A4 event 867 is sensed as indicated by A4 event marker 886, after the extended A4 refractory period 882. Control circuit 206 effectively induces one cycle of ventricular asystole (assuming AV conduction block) by extending the A4 refractory period 882 and the LR interval 885 for one cardiac cycle. By inducing one cycle of ventricular asystole, the A1, A2 and A3 events are removed from the motion sensor signal 854. Any event detected from the motion sensor signal 854 after the extended A4 refractory period is an A4 event with high certainty.

If the non-refractory A4 event 886 is near the end of the extended LR interval 885, A4 tracking is confirmed. The A4 event is occurring at close to twice the median ventricular event interval since the previous A4 event detection 876 and ventricular pacing pulse 878, indicating that the median ventricular event interval properly tracked the atrial events. The A4 event detection 876 is confirmed to be a true A4 event detection based on the late occurrence of the A4 event detection 886 after extended A4 refractory period 882.

In some examples, if the A4 event occurs after an A4 event confirmation interval 887, which may be 200 ms (or other predetermined interval) shorter than the extended LR interval 885, A4 tracking is confirmed. The A4 refractory period 872 is restored in response to confirming A4 tracking and is started upon the next ventricular event. Control circuit 206 returns to atrial synchronized ventricular pacing by setting an AV interval in response to the next detected A4 event 890 and delivers a subsequent ventricular pacing pulse 892.

If the first non-refractory A4 event detection 886 occurs earlier during the extended LR interval 885, for example before the A4 confirmation interval 887 expires, A4 tracking is not confirmed by control circuit 206. The previously tracked motion sensor signal may be an A3 event, that is now masked by the extended A4 refractory period, thereby unmasking the true A4 event. An early A4 detection after the extended A4 refractory period may be indicative of A3 oversensing or oversensing of other motion sensor signal noise, such as patient activity or environmental vibrations. Control circuit 206 may temporarily limit the maximum atrial tracking rate by maintaining the extended A4 refractory period 882 for a predetermined number of cardiac cycles to promote proper A4 event tracking as described above in conjunction with FIG. 13. Additionally or alternatively, control circuit 206 may take corrective action by adjusting one or more A4 event detection control parameters to promote more reliable A4 event detection and tracking as described in conjunction with FIG. 13.

Figure 15:
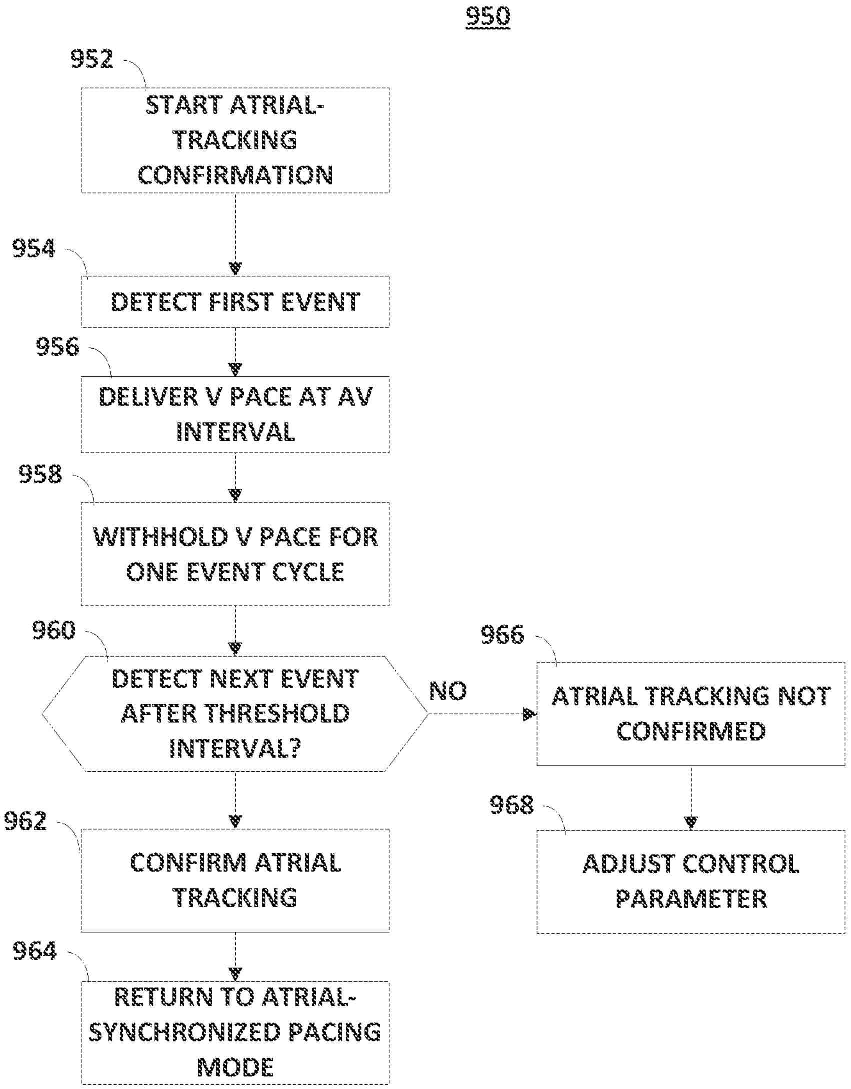
FIG. 15 is a flow chart of a method for confirming atrial-tracking of ventricular pacing pulses delivered by an intracardiac ventricular pacemaker according to one example.

FIG. 15 is a flow chart 950 of a method for confirming atrial-tracking of ventricular pacing pulses delivered by pacemaker 14 according to one example. Pacemaker 14 may be operating in an atrial-synchronized ventricular pacing mode based on events detected from the motion sensor signal and start an atrial tracking confirmation process at block 952. As described above, the atrial-tracking confirmation process may be started in response to a ventricular rate reaching or exceeding an atrial-tracking confirmation threshold rate.

At block 954, a first event is detected from the motion sensor signal outside an applied A4 refractory period. The A4 refractory period may be based on a median ventricular event interval as described above. A ventricular pacing pulse is delivered at block 956 after an AV interval following the detected first event. At block 958, a ventricular pacing pulse is withheld for one event cycle of the motion sensor signal. In the illustrative example of the A4 tracking confirmation process presented in conjunction with FIG. 13, the control circuit 206 of pacemaker 14 withholds or inhibits a ventricular pacing pulse by extending the A4 refractory period (forcing the next expected event detection to be a refractory event) and extending the LR interval to greater than twice the median ventricular event interval. It is recognized that other techniques may be used to cause the pacemaker 14 to withhold or delay a ventricular pacing pulse for at least one event cycle of the motion sensor signal to enable A4 detection with high certainty in the absence of ventricular motion sensor signal events.

For instance, a second event of the motion sensor signal after the ventricular pacing pulse is delivered at block 956 may be ignored by control circuit 206 in order to withhold the next ventricular pacing pulse at block 958. In another example, the control circuit 206 may switch the pacing mode for one pacing cycle to an OVO mode to promote detection of motion sensor signal events during at least one atrial cycle in which a ventricular pacing pulse is withheld to cause ventricular asystole for the one atrial cycle. By withholding the atrial-synchronized ventricular pacing pulse for one cycle of the motion sensor signal, the ventricular motion sensor signal events, A1, A2 and A3, are removed from the motion sensor signal as indicated during the baseline interval 875 of FIG. 14. This facilitates detection of the next event being a true A4 event with high certainty due to the absence of confounding ventricular events in the motion sensor signal.

The timing of the next detected event following a withheld ventricular pacing pulse enables control circuit 206 to confirm that a preceding detected event is an A4 event and confirm atrial tracking of the delivered ventricular pacing pulses. If the next detected event after withholding the pacing pulse occurs after a threshold time interval after the pacing pulse delivered at block 956, atrial tracking is confirmed at block 962. In other examples, if the next detected event at block 960 occurs at approximately twice the median ventricular event interval since the first motion sensor signal event was detected at block 954, the first event detected at block 954 is confirmed to be an atrial A4 event. The detected events are occurring at a rate that matches the median ventricular event interval indicating a true atrial rate that was properly tracked by ventricular pacing pulse. A4 tracking is confirmed at block 962. Pacemaker 14 may return to the atrial-synchronized ventricular pacing mode at block 964.

In some examples, the timing of a detected event from the motion sensor signal following a withheld ventricular pacing pulse is compared to a ventricular rate interval by detecting a first event from the motion senor signal, delivering a ventricular pacing pulse synchronized to the first event, starting a LR interval in response to the delivered ventricular pacing pulse that is twice a median ventricular event interval, ignoring the next, second motion senor signal event (e.g., by extending the A4 refractory period) in order to withhold the next atrial-synchronized ventricular pacing pulse, then determining if a third event detected from the motion sensor signal, which is an A4 event with high confidence, occurs at approximately twice the ventricular event interval after the first detected event.

While this process is one implementation for confirming A4 tracking of delivered ventricular pacing pulses based on the timing of a detected motion sensor signal event following a withheld or delayed ventricular pacing pulse, other methods may be used for confirming A4 tracking based on the timing of a detected motion sensor signal event after inducing one cardiac cycle of ventricular asystole. For example, the time interval from the first detected event to the second refractory event and from the second refractory event to the third detected event may be compared to a previously determined median ventricular event interval. The time interval between the first detected event and the third detected event may be compared to twice the preceding median ventricular event interval. If the time intervals separating the first, second and/or third events correspond to a median ventricular event interval determined during atrial-synchronized ventricular pacing, the first, second and third events of the motion sensor signal during the atrial-tracking confirmation process are confirmed as atrial events occurring at the previous atrial-tracked ventricular pacing rate. Atrial-tracking of the ventricular pacing pulses can be confirmed based on confirmation of at least one of the detected events from the motion sensor signal being an atrial event. The rate of the events detected from the motion sensor signal would not change when a ventricular pacing pulse is withheld if the detected events are true atrial events.

If the earliest event detected at block 960 from the motion sensor signal after the withheld ventricular pacing pulse occurs earlier than the expiration of the threshold interval since the ventricular pacing pulse delivered at block 956, atrial tracking is not confirmed at block 966. As indicated above, the threshold interval may be based on the median ventricular rate interval determined during the atrial-synchronized ventricular pacing mode. The time from the first event to the event detected at block 960 is not correlated to the ventricular event rate, indicating a change in the detected event rate when the ventricular pacing pulse is withheld. This change indicates that detected events prior to the withheld pacing pulse were not true atrial A4 events.

At block 968, the control circuit 206 may adjust a control parameter to avoid improper event tracking of the ventricular pacing pulses. The control circuit 206 may adjust the A4 refractory period, set a minimum A4 refractory period to limit the maximum tracking ventricular pacing rate, adjust the A4 detection threshold amplitude, adjust the A3 detection threshold amplitude, adjust a T-wave sensing parameter, and/or adjust a start time and/or end time of the A3 time window. Control parameter adjustment at block 968 promotes reliable A4 event detection from the motion sensor signal, without A3 or other noise oversensing, and proper atrial tracking of the ventricular pacing pulses delivered by pacemaker 14.

Various examples of an intracardiac ventricular pacemaker configured to deliver atrial-synchronized ventricular pacing have been described according to illustrative embodiments. The intracardiac ventricular pacemaker is configured to detect A4 events from a motion sensor signal for controlling the atrial-synchronized ventricular pacing according to various methods described above. The methods may include an A4 tracking confirmation process to interrupt tracking of oversensed, non-A4 events that may lead to an accelerated ventricular pacing rate and restore proper atrial A4 event tracking of ventricular pacing pulses.

It should be understood that, depending on the example, certain acts or events of any of the methods described herein can be performed in a different sequence, may be added, merged, or left out all together (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single module or unit for purposes of clarity, it should be understood that the techniques of this disclosure may be performed by a combination of units or modules associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a pacemaker has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

The invention claimed is:

1. A medical device comprising:

a pulse generator configured to deliver ventricular pacing pulses;

a motion sensor configured to sense a motion signal;

a control circuit in communication with the motion sensor and the pulse generator and configured to:

apply a first post-ventricular atrial refractory period to the motion signal in response to a delivered ventricular pacing pulse of the ventricular pacing pulses delivered by the pulse generator;

determine that a rate of the delivered ventricular pacing pulses is greater than a threshold rate;

apply a second post-ventricular atrial refractory period to the motion signal in response to determining that the rate of the delivered ventricular pacing pulses is greater than the threshold rate, the second post-ventricular atrial refractory period being greater than the first post-ventricular atrial refractory period;

sense a non-refractory atrial event signal from the motion signal after the second post-ventricular atrial refractory period; and based on a time of the non-refractory atrial event signal sensed after the second post-ventricular atrial refractory period, select one of the first post-ventricular atrial refractory period or the second post-ventricular atrial refractory period;

the pulse generator further configured to deliver a first subsequent ventricular pacing pulse in response to the non-refractory atrial event signal being sensed after the second post-ventricular atrial refractory period;

the control circuit further configured to:

apply the selected one of the first post-ventricular atrial refractory period or the second post-ventricular atrial refractory period to the motion signal following the first subsequent ventricular pacing pulse; and sense a second non-refractory atrial event signal from the motion signal after the selected one of the first post-ventricular atrial refractory period or the second post-ventricular atrial refractory period; and the pulse generator further configured to deliver a second subsequent ventricular pacing pulse in response to the second non-refractory atrial event signal being sensed by the control circuit.

2. The medical device of claim 1 wherein the control circuit is further configured to control the pulse generator to deliver each of a plurality of the ventricular pacing pulses by:

applying the first post-ventricular atrial refractory period;

sensing an atrial event signal from the motion signal after the first post-ventricular atrial refractory period; and in response to sensing the atrial event signal, controlling the pulse generator to deliver a ventricular pacing pulse of the plurality of the ventricular pacing pulses.

3. The medical device of claim 2 wherein the control circuit is further configured to determine the second post-ventricular atrial blanking period by:

determining a ventricular to atrial event time interval extending from one of the delivered ventricular pacing pulses to one of the atrial event signals sensed from the motion signal after the first post-ventricular atrial refractory period; and determining the second post-ventricular atrial blanking period based on the determined ventricular to atrial event time interval.

4. The medical device of claim 1 wherein the control circuit is further configured to:

based on the time of the non-refractory atrial event signal, select one of the first post-ventricular atrial refractory period or the second post-ventricular atrial refractory period to be applied following at least one subsequent ventricular pacing pulse by:

when the non-refractory atrial event signal is not sensed later than a tracking confirmation time interval, apply the second post-ventricular atrial refractory period following at least one subsequent ventricular pacing pulse; and when the non-refractory atrial event signal is sensed later than the tracking confirmation time interval, restore the first post-ventricular atrial refractory period.

5. The medical device of claim 4 wherein the control circuit is further configured to increase an oversense counter when the non-refractory atrial event signal is not sensed later than the tracking confirmation time interval.

6. The medical device of claim 1 wherein the control circuit is further configured to:

apply a tracking confirmation time interval in response to detecting the rate of the ventricular pacing pulses being greater than the threshold rate; and determine the time of the non-refractory atrial event signal by determining if the non-refractory atrial event signal sensed after the second post-ventricular atrial refractory period is sensed later than the tracking confirmation time interval.

7. The medical device of claim 6 wherein the control circuit is further configured to:

determine a ventricular rate interval from the delivered ventricular pacing pulses; and determine the tracking confirmation time interval based on twice the ventricular rate interval.

8. The medical device of claim 1 wherein the control circuit is further configured to:

determine a ventricular rate interval from the delivered ventricular pacing pulses;

determine an extended lower rate interval based on the ventricular rate interval; and start the extended lower rate interval and the second post-ventricular atrial refractory period upon a delivered ventricular pacing pulse in response to determining that the rate of the delivered ventricular pacing pulses is greater than the threshold rate.

9. The medical device of claim 8 wherein the control circuit is further configured to:

determine the ventricular rate interval by determining a median ventricular rate interval; and determine the extended lower rate interval based on twice the median ventricular rate interval.

10. The medical device of claim 1 further comprising:

a housing enclosing the pulse generator, the motion sensor and the control circuit; and at least one pair of electrodes on the housing for delivering the ventricular pacing pulses.

11. A method comprising:

delivering ventricular pacing pulses;

sensing a motion signal;

applying a first post-ventricular atrial refractory period to the motion signal in response to a delivered ventricular pacing pulse;

determining that a rate of the delivered ventricular pacing pulses is greater than a threshold rate;

applying a second post-ventricular atrial refractory period to the motion signal in response to determining that the rate of the delivered ventricular pacing pulses is greater than the threshold rate, the second post-ventricular atrial refractory period being longer than the first post-ventricular atrial refractory period;

sensing a non-refractory atrial event signal from the motion signal after the second post-ventricular atrial refractory period;

based on a time of the sensed non-refractory atrial event signal after the second post-ventricular atrial refractory period, selecting one of the first post-ventricular atrial refractory period or the second post-ventricular atrial refractory period;

delivering a first subsequent ventricular pacing pulse in response to the non-refractory atrial event signal being sensed after the second post-ventricular atrial refractory period;

applying the selected one of the first post-ventricular atrial refractory period or the second post-ventricular atrial refractory period to the motion signal following the first subsequent ventricular pacing pulse;

sensing a second non-refractory atrial event signal from the motion signal after the selected one of the first post-ventricular atrial refractory period or the second post-ventricular atrial refractory period; and delivering a second subsequent ventricular pacing pulse in response to the second non-refractory atrial event signal being sensed.

12. The method of claim 11 delivering each of a plurality of the ventricular pacing pulses comprises:

applying the first post-ventricular atrial refractory period;

sensing an atrial event signal from the motion signal after the first post-ventricular atrial refractory period; and in response to sensing the atrial event signal, delivering a ventricular pacing pulse of the plurality of the ventricular pacing pulses.

13. The method of claim 12 further comprising determining the second post-ventricular atrial blanking period by:

determining a ventricular to atrial event time interval extending from one of the delivered ventricular pacing pulses to one of the atrial event signals sensed from the motion signal after the first post-ventricular atrial refractory period; and determining the second post-ventricular atrial blanking period based on the determined ventricular to atrial event time interval.

14. The method of claim 11 further comprising:

based on the time of the non-refractory atrial event signal, selecting one of the first post-ventricular atrial refractory period or the second post-ventricular atrial refractory period to be applied following at least one subsequent ventricular pacing pulse by:

when the non-refractory atrial event signal is not sensed later than a tracking confirmation time interval, applying the second post-ventricular atrial refractory period following at least one subsequent ventricular pacing pulse; and when the non-refractory atrial event signal is sensed later than the tracking confirmation time interval, restoring the first post-ventricular atrial refractory period.

15. The method of claim 14 further comprising increasing an oversense counter when the non-refractory atrial event signal is not sensed later than the tracking confirmation time interval.

16. The method of claim 11 further comprising:

applying a tracking confirmation time interval in response to detecting the rate of the ventricular pacing pulses being greater than the threshold rate; and determining the time of the non-refractory atrial event signal by determining if the non-refractory atrial event signal sensed after the second post-ventricular atrial refractory period is sensed later than the tracking confirmation time interval.

17. The method of claim 16 further comprising:

determining a ventricular rate interval from the delivered ventricular pacing pulses; and determining the tracking confirmation time interval based on twice the ventricular rate interval.

18. The method of claim 11 wherein the control circuit is further configured to:

determining a ventricular rate interval from the delivered ventricular pacing pulses;

determining an extended lower rate interval based on the ventricular rate interval; and starting the extended lower rate interval and the second post-ventricular atrial refractory period upon a delivered ventricular pacing pulse in response to determining that the rate of the delivered ventricular pacing pulses is greater than the threshold rate.

19. The method of claim 18 further comprising:

determining the ventricular rate interval by determining a median ventricular rate interval; and determining the extended lower rate interval based on twice the median ventricular rate interval.

20. A non-transitory computer readable medium storing a set of instructions that, when executed by a control circuit of a medical device, cause the device to:

deliver ventricular pacing pulses;

sense a motion signal;

apply a first post-ventricular atrial refractory period to the motion signal in response to a delivered ventricular pacing pulse;

determine that a rate of the delivered ventricular pacing pulses is greater than a threshold rate;

apply a second post-ventricular atrial refractory period to the motion signal in response to determining that the rate of the delivered ventricular pacing pulses is greater than the threshold rate, the second post-ventricular atrial refractory period being longer than the first post-ventricular atrial refractory period;

sense a non-refractory atrial event signal from the motion signal after the second post-ventricular atrial refractory period;

based on a time of the sensed non-refractory atrial event signal after the second post-ventricular atrial refractory period, select one of the first post-ventricular atrial refractory period or the second post-ventricular atrial refractory period;

deliver a first subsequent ventricular pacing pulse in response to the non-refractory atrial event signal being sensed after the second post-ventricular atrial refractory period;

apply the selected one of the first post-ventricular atrial refractory period or the second post-ventricular atrial refractory period to the motion signal following the first subsequent ventricular pacing pulse;

sense a second non-refractory atrial event signal from the motion signal after the selected one of the first post-ventricular atrial refractory period or the second post-ventricular atrial refractory period; and deliver a second subsequent ventricular pacing pulse in response to the second non-refractory atrial event signal being sensed.

* * * * *